(12) United States Patent
Pelot et al.

(10) Patent No.: US 9,422,018 B2
(45) Date of Patent: Aug. 23, 2016

(54) SEAT POST

(71) Applicant: Fox Factory, Inc., Scotts Valley, CA (US)

(72) Inventors: Sante Pelot, Freiburg (DE); David M. Haugen, Pacific Grove, CA (US); Wes Allinger, Santa Cruz, CA (US); Mario Galasso, Sandy Hook, CT (US); Andrew Laird, Los Gatos, CA (US)

(73) Assignee: Fox Factory, Inc., Scotts Valley, CA (US)

( * ) Notice: Subject to any disclaimer, the term of this patent is extended or adjusted under 35 U.S.C. 154(b) by 527 days.

(21) Appl. No.: 13/844,516

(22) Filed: Mar. 15, 2013

(65) Prior Publication Data

US 2013/0221713 A1 Aug. 29, 2013

Related U.S. Application Data

(63) Continuation-in-part of application No. 12/626,384, filed on Nov. 25, 2009, now Pat. No. 9,108,098, which is a continuation-in-part of application No. 13/292,949, filed on Nov. 9, 2011, now abandoned, (Continued)

(51) Int. Cl.

| | |
|---|---|
| *B62J 1/00* | (2006.01) |
| *B62J 1/02* | (2006.01) |
| *B62K 19/36* | (2006.01) |
| *G06F 19/00* | (2011.01) |
| *B62J 1/08* | (2006.01) |

(52) U.S. Cl.
CPC . *B62J 1/02* (2013.01); *B62K 19/36* (2013.01); *B62J 2001/085* (2013.01); *G06F 19/3481* (2013.01)

(58) Field of Classification Search
CPC .......................................................... F16B 7/10
See application file for complete search history.

(56) References Cited

U.S. PATENT DOCUMENTS

| | | | |
|---|---|---|---|
| 1,948,600 | A | 2/1934 | Templeton |
| 2,259,437 | A | 10/1941 | Dean |
| 2,492,331 | A | 12/1949 | Spring |
| 2,540,525 | A | 2/1951 | Howarth et al. |
| 2,697,600 | A | 12/1954 | Gregoire |
| 2,705,119 | A | 3/1955 | Ingwer |

(Continued)

FOREIGN PATENT DOCUMENTS

| | | |
|---|---|---|
| DE | 202010012738 U1 | 12/2010 |
| EP | 304801 A2 | 3/1989 |

(Continued)

OTHER PUBLICATIONS

European Search Report, European Patent Application No. 14189773.6, May 4, 2015, 4 Pages.

(Continued)

*Primary Examiner* — Jonathan M Dager

(57) ABSTRACT

A system including: a seat post; a user interface operatively connected with the seat post, the user interface configured for receiving instructions associated with a height of the seat post and for communicating received instructions to at least one controller coupled with a motive source of the seat post; and a valve assembly in communication with the motive source, the valve assembly regulating fluid flow within a variable finite positioning seat post height mode in response to a translation of the received instructions by the motive source.

24 Claims, 18 Drawing Sheets

Related U.S. Application Data which is a continuation-in-part of application No. 13/022,346, filed on Feb. 7, 2011, which is a continuation-in-part of application No. 12/727,915, filed on Mar. 19, 2010, now Pat. No. 9,140,325, and a continuation-in-part of application No. 12/773,671, filed on May 4, 2010, now abandoned, which is a continuation-in-part of application No. 13/176,336, filed on Jul. 5, 2011, now Pat. No. 8,814,109.

(60) Provisional application No. 61/638,406, filed on Apr. 25, 2012, provisional application No. 61/117,608, filed on Nov. 25, 2008, provisional application No. 61/533,712, filed on Sep. 12, 2011, provisional application No. 61/302,070, filed on Feb. 5, 2010, provisional application No. 61/161,552, filed on Mar. 19, 2009, provisional application No. 61/161,620, filed on Mar. 19, 2009, provisional application No. 61/175,422, filed on May 4, 2009, provisional application No. 61/361,376, filed on Jul. 2, 2010.

(56) References Cited

U.S. PATENT DOCUMENTS

| | | |
|---|---|---|
| 2,784,962 A | 3/1957 | Sherburne |
| 2,879,971 A | 3/1959 | Demay |
| 2,991,804 A | 7/1961 | Merkle |
| 3,087,583 A | 4/1963 | Bruns |
| 3,206,153 A | 9/1965 | Burke |
| 3,284,076 A | 11/1966 | Gibson |
| 3,528,700 A | 9/1970 | Janu et al. |
| 3,560,033 A | 2/1971 | Barkus |
| 3,650,033 A | 3/1972 | Behne et al. |
| 3,701,544 A | 10/1972 | Stankovich |
| 3,830,482 A | 8/1974 | Norris |
| 4,103,881 A | 8/1978 | Simich |
| 4,348,016 A | 9/1982 | Milly |
| 4,474,363 A | 10/1984 | Numazawa et al. |
| 4,744,444 A | 5/1988 | Gillingham |
| 4,773,671 A | 9/1988 | Inagaki |
| 4,830,395 A | 5/1989 | Foley |
| 4,836,578 A | 6/1989 | Soltis |
| 4,949,989 A | 8/1990 | Kakizaki et al. |
| 4,984,819 A | 1/1991 | Kakizaki et al. |
| 5,027,303 A | 6/1991 | Witte |
| 5,044,614 A | 9/1991 | Rau |
| 5,060,959 A | 10/1991 | Davis et al. |
| 5,105,918 A | 4/1992 | Hagiwara et al. |
| 5,152,547 A | 10/1992 | Davis |
| 5,203,584 A | 4/1993 | Butsuen et al. |
| 5,236,169 A | 8/1993 | Johnsen et al. |
| 5,265,902 A | 11/1993 | Lewis |
| 5,348,112 A | 9/1994 | Vaillancourt |
| 5,390,949 A | 2/1995 | Naganathan et al. |
| 5,542,150 A | 8/1996 | Tu |
| 5,551,674 A | 9/1996 | Johnsen |
| 5,553,836 A | 9/1996 | Ericson |
| 5,592,401 A | 1/1997 | Kramer |
| 5,598,337 A | 1/1997 | Butsuen et al. |
| 5,722,645 A | 3/1998 | Reitter |
| 5,803,443 A | 9/1998 | Chang |
| 5,826,935 A * | 10/1998 | DeFreitas ............... B62K 19/36 248/404 |
| 5,850,352 A | 12/1998 | Moezzi et al. |
| 5,954,318 A | 9/1999 | Kluhsman |
| 5,971,116 A | 10/1999 | Franklin |
| 6,013,007 A | 1/2000 | Root et al. |
| 6,035,979 A | 3/2000 | Foerster |
| 6,058,340 A | 5/2000 | Uchiyama et al. |
| 6,073,736 A | 6/2000 | Franklin |
| 6,135,434 A | 10/2000 | Marking |
| 6,244,398 B1 | 6/2001 | Girvin et al. |
| 6,254,067 B1 | 7/2001 | Yih |
| 6,311,962 B1 | 11/2001 | Marking |
| 6,343,807 B1 | 2/2002 | Rathbun |
| 6,360,857 B1 | 3/2002 | Fox et al. |
| 6,378,816 B1 | 4/2002 | Pfister |
| 6,389,341 B1 | 5/2002 | Davis |
| 6,390,747 B1 | 5/2002 | Commins |
| 6,427,812 B2 | 8/2002 | Crawley et al. |
| 6,434,460 B1 | 8/2002 | Uchino et al. |
| 6,592,136 B2 | 7/2003 | Becker et al. |
| 6,609,686 B2 | 8/2003 | Malizia |
| 6,623,389 B1 | 9/2003 | Campagnolo |
| 6,732,033 B2 | 5/2004 | LaPlante et al. |
| 6,837,827 B1 | 1/2005 | Lee et al. |
| 6,853,955 B1 | 2/2005 | Burrell et al. |
| 6,857,625 B2 | 2/2005 | Löser et al. |
| 6,863,291 B2 | 3/2005 | Miyoshi |
| 6,902,513 B1 | 6/2005 | McClure et al. |
| 6,921,351 B1 | 7/2005 | Hickman et al. |
| 6,935,157 B2 | 8/2005 | Miller |
| 6,991,076 B2 | 1/2006 | McAndrews |
| 7,025,367 B2 * | 4/2006 | McKinnon ............. B62K 19/36 267/132 |
| 7,076,351 B2 | 7/2006 | Hamilton et al. |
| 7,128,192 B2 | 10/2006 | Fox |
| 7,128,693 B2 | 10/2006 | Brown et al. |
| 7,135,794 B2 | 11/2006 | Kühnel |
| 7,163,222 B2 | 1/2007 | Becker et al. |
| 7,204,466 B2 | 4/2007 | Hsieh |
| 7,217,224 B2 | 5/2007 | Thomas |
| 7,287,760 B1 | 10/2007 | Quick et al. |
| 7,289,138 B2 | 10/2007 | Foote et al. |
| 7,292,867 B2 | 11/2007 | Werner et al. |
| 7,293,764 B2 | 11/2007 | Fang |
| 7,306,206 B2 | 12/2007 | Turner |
| 7,316,406 B2 | 1/2008 | Kimura et al. |
| 7,363,129 B1 | 4/2008 | Barnicle et al. |
| 7,374,028 B2 | 5/2008 | Fox |
| 7,397,355 B2 | 7/2008 | Tracy |
| 7,469,910 B2 | 12/2008 | Münster et al. |
| 7,484,603 B2 | 2/2009 | Fox |
| 7,490,705 B2 | 2/2009 | Fox |
| 7,581,743 B2 | 9/2009 | Graney et al. |
| 7,631,882 B2 | 12/2009 | Hirao et al. |
| 7,673,936 B2 * | 3/2010 | Hsu ............................ B62J 1/08 297/215.13 |
| 7,694,987 B2 | 4/2010 | McAndrews |
| 7,699,753 B2 | 4/2010 | Daikeler et al. |
| 7,726,042 B2 | 6/2010 | Meschan |
| 7,736,272 B2 | 6/2010 | Martens |
| 7,837,213 B2 | 11/2010 | Colegrove et al. |
| 7,840,346 B2 | 11/2010 | Huhtala et al. |
| 7,841,258 B2 | 11/2010 | Komatsu et al. |
| 7,845,602 B1 | 12/2010 | Young et al. |
| 7,857,325 B2 | 12/2010 | Copsey et al. |
| 7,901,292 B1 | 3/2011 | Uhlir et al. |
| 7,909,348 B2 | 3/2011 | Klieber et al. |
| 7,931,563 B2 | 4/2011 | Shaw et al. |
| 8,016,349 B2 * | 9/2011 | Mouri ......................... B62J 1/08 297/215.13 |
| 8,042,427 B2 | 10/2011 | Kawakami et al. |
| 8,087,676 B2 | 1/2012 | McIntyre |
| 8,091,910 B2 | 1/2012 | Hara et al. |
| 8,127,900 B2 | 3/2012 | Inoue |
| 8,136,877 B2 * | 3/2012 | Walsh ......................... B62J 1/06 297/215.13 |
| 8,191,964 B2 | 6/2012 | Hsu et al. |
| 8,201,476 B2 | 6/2012 | Tsumiyama |
| 8,210,106 B2 | 7/2012 | Tai et al. |
| 8,246,065 B1 | 8/2012 | Kodama et al. |
| 8,256,732 B1 | 9/2012 | Young et al. |
| 8,262,100 B2 | 9/2012 | Thomas |
| 8,286,982 B2 | 10/2012 | Plantet et al. |
| 8,292,274 B2 | 10/2012 | Adoline et al. |
| 8,308,124 B2 * | 11/2012 | Hsu ............................. B62J 1/08 248/161 |
| 8,317,261 B2 * | 11/2012 | Walsh ......................... B62J 1/10 297/215.13 |
| 8,328,454 B2 | 12/2012 | McAndrews et al. |
| 8,336,683 B2 | 12/2012 | McAndrews et al. |
| 8,430,770 B2 | 4/2013 | Dugan et al. |

(56) References Cited

U.S. PATENT DOCUMENTS

| | | | |
|---|---|---|---|
| 8,458,080 B2 | 6/2013 | Shirai | |
| 8,550,551 B2 | 10/2013 | Shirai | |
| 8,596,663 B2* | 12/2013 | Shirai | B62J 19/36 188/275 |
| 8,641,073 B2 | 2/2014 | Lee et al. | |
| 8,727,947 B2 | 5/2014 | Tagliabue | |
| 8,744,699 B2 | 6/2014 | Yamaguchi et al. | |
| 8,781,680 B2* | 7/2014 | Ichida | B62J 99/00 701/37 |
| 8,781,690 B2* | 7/2014 | Hara | B62J 1/08 701/49 |
| 8,814,109 B2 | 8/2014 | Calendrille et al. | |
| 8,833,786 B2 | 9/2014 | Camp et al. | |
| 8,845,496 B2 | 9/2014 | Arrasvuori et al. | |
| 8,888,115 B2* | 11/2014 | Chubbuck | B62K 19/36 267/132 |
| 8,950,771 B2* | 2/2015 | Felsl | B62J 1/08 280/281.1 |
| 8,967,343 B2* | 3/2015 | Battlogg | B62K 25/04 188/266.2 |
| 9,073,592 B2* | 7/2015 | Hsu | B62J 1/08 |
| 9,108,098 B2 | 8/2015 | Galasso et al. | |
| 9,126,647 B2* | 9/2015 | Kuo | B62J 1/08 |
| 9,140,325 B2 | 9/2015 | Cox et al. | |
| 9,157,523 B2* | 10/2015 | Miki | F16H 59/044 |
| 9,199,690 B2* | 12/2015 | Watarai | B62J 99/00 |
| 2002/0032508 A1 | 3/2002 | Uchino et al. | |
| 2002/0050112 A1 | 5/2002 | Koch et al. | |
| 2002/0089107 A1 | 7/2002 | Koh | |
| 2002/0185581 A1* | 12/2002 | Trask | B62J 1/08 248/408 |
| 2002/0187867 A1 | 12/2002 | Ichida et al. | |
| 2003/0001358 A1 | 1/2003 | Becker et al. | |
| 2003/0040348 A1 | 2/2003 | Martens et al. | |
| 2003/0054327 A1 | 3/2003 | Evensen et al. | |
| 2003/0065430 A1 | 4/2003 | Lu et al. | |
| 2003/0160369 A1 | 8/2003 | LaPlante et al. | |
| 2004/0004659 A1 | 1/2004 | Foote et al. | |
| 2004/0075350 A1 | 4/2004 | Kuhnel | |
| 2004/0103146 A1 | 5/2004 | Park | |
| 2004/0208687 A1* | 10/2004 | Sicz | B62J 1/08 403/109.3 |
| 2004/0256778 A1 | 12/2004 | Verriet | |
| 2005/0110229 A1 | 5/2005 | Kimura et al. | |
| 2005/0239601 A1 | 10/2005 | Thomas | |
| 2005/0288154 A1 | 12/2005 | Lee et al. | |
| 2006/0040793 A1 | 2/2006 | Martens | |
| 2006/0064223 A1 | 3/2006 | Voss | |
| 2006/0066074 A1* | 3/2006 | Turner | B23K 19/36 280/287 |
| 2006/0136173 A1 | 6/2006 | Case et al. | |
| 2006/0163787 A1 | 7/2006 | Munster et al. | |
| 2006/0175792 A1* | 8/2006 | Sicz | B62J 1/06 280/200 |
| 2006/0213082 A1 | 9/2006 | Meschan | |
| 2006/0253210 A1 | 11/2006 | Rosenberg | |
| 2006/0289258 A1 | 12/2006 | Fox | |
| 2007/0006489 A1 | 1/2007 | Case et al. | |
| 2007/0008096 A1 | 1/2007 | Tracy | |
| 2007/0032981 A1 | 2/2007 | Merkel et al. | |
| 2007/0070069 A1 | 3/2007 | Samarasekera et al. | |
| 2007/0213126 A1 | 9/2007 | Deutsch et al. | |
| 2007/0239479 A1 | 10/2007 | Arrasvuori et al. | |
| 2008/0018065 A1 | 1/2008 | Hirao et al. | |
| 2008/0093820 A1 | 4/2008 | McAndrews | |
| 2008/0099968 A1 | 5/2008 | Schroeder | |
| 2008/0116622 A1* | 5/2008 | Fox | B62K 25/08 267/64.28 |
| 2008/0163718 A1 | 7/2008 | Chiang | |
| 2008/0200310 A1 | 8/2008 | Tagliabue | |
| 2008/0303320 A1* | 12/2008 | Schranz | B62J 1/08 297/215.14 |
| 2009/0121398 A1 | 5/2009 | Inoue | |
| 2009/0192673 A1* | 7/2009 | Song | B62K 21/08 701/37 |
| 2009/0236807 A1 | 9/2009 | Wootten et al. | |
| 2009/0261542 A1 | 10/2009 | McIntyre | |
| 2009/0277736 A1 | 11/2009 | McAndrews et al. | |
| 2009/0324327 A1* | 12/2009 | McAndrews | B62J 1/08 403/409.1 |
| 2010/0010709 A1 | 1/2010 | Song | |
| 2010/0044975 A1 | 2/2010 | Yablon et al. | |
| 2010/0139442 A1 | 6/2010 | Tsumiyama | |
| 2010/0160014 A1 | 6/2010 | Galasso et al. | |
| 2010/0207351 A1* | 8/2010 | Klieber | B62K 19/36 280/278 |
| 2010/0244340 A1 | 9/2010 | Wootten et al. | |
| 2010/0252972 A1 | 10/2010 | Cox et al. | |
| 2010/0276906 A1 | 11/2010 | Galasso et al. | |
| 2010/0308628 A1* | 12/2010 | Hsu | B62K 19/36 297/215.14 |
| 2010/0314917 A1* | 12/2010 | Hsieh | B29K 19/36 297/215.13 |
| 2010/0327542 A1* | 12/2010 | Hara | B62J 99/00 280/5.503 |
| 2011/0095507 A1 | 4/2011 | Plantet et al. | |
| 2011/0097139 A1* | 4/2011 | Hsu | B62J 1/06 403/109.1 |
| 2011/0109060 A1 | 5/2011 | Earle et al. | |
| 2011/0202236 A1 | 8/2011 | Galasso et al. | |
| 2011/0204201 A1* | 8/2011 | Kodama | B62J 1/08 248/406.1 |
| 2011/0257848 A1* | 10/2011 | Shirai | B62K 19/36 701/49 |
| 2012/0006949 A1* | 1/2012 | Laird | B62J 1/08 248/161 |
| 2012/0080279 A1 | 4/2012 | Galasso et al. | |
| 2012/0228906 A1* | 9/2012 | McAndrews | B62J 1/08 297/215.13 |
| 2012/0253599 A1 | 10/2012 | Shirai | |
| 2012/0274043 A1* | 11/2012 | Lee | B62K 19/36 280/288.4 |
| 2013/0090195 A1* | 4/2013 | Yamaguchi | B60T 7/102 474/80 |
| 2013/0119634 A1* | 5/2013 | Camp | B62J 1/08 280/287 |
| 2014/0061419 A1* | 3/2014 | Wehage | B62J 1/06 248/404 |
| 2015/0197308 A1* | 7/2015 | Butora | B62K 25/10 280/283 |
| 2015/0291248 A1 | 10/2015 | Fukao et al. | |

FOREIGN PATENT DOCUMENTS

| | | |
|---|---|---|
| EP | 1241087 A1 | 9/2002 |
| EP | 1355209 A1 | 10/2003 |
| JP | 57173632 U | 11/1982 |
| JP | 57182506 A | 11/1982 |
| JP | 01106721 A | 4/1989 |
| JP | 04-203540 | 7/1992 |
| JP | 05-149364 | 6/1993 |
| WO | 98/40231 | 9/1998 |
| WO | 99/06231 | 2/1999 |

OTHER PUBLICATIONS

"European Search Report and Written Opinion, European Patent Application No. 13165362.8", Sep. 16, 2014, 6 Pages.

"European Patent Office Final Decision dated Mar. 21, 2013", European Patent Application No. 10161906.2.

* cited by examiner

SEAT POST

CROSS-REFERENCE TO RELATED APPLICATIONS

This application claims the benefit of and claims priority of U.S. Provisional Patent Application Ser. No. 61/638,406, filed on Apr. 25, 2012, entitled "PERFORMANCE BASED HARDWARE CONFIGURATION" by Haugen et al., assigned to the assignee of the present application, and is hereby incorporated by reference in its entirety.

This application is a continuation in part of and claims the benefit of co-pending U.S. patent application Ser. No. 12/626,384, filed on Nov. 25, 2009, entitled "METHODS AND APPARATUS FOR VIRTUAL COMPETITION", by Galasso et al., assigned to the assignee of the present application, which is incorporated herein by reference in its entirety.

The application with Ser. No. 12/626,384 claims the benefit of and claims priority of U.S. Provisional Patent Application Ser. No. 61/117,608, filed on Nov. 25, 2008, entitled "METHODS AND APPARATUS FOR VIRTUAL COMPETITION" by Galasso et al., assigned to the assignee of the present application, and is hereby incorporated by reference in its entirety herein.

This application is a continuation in part of and claims the benefit of co-pending U.S. patent application Ser. No. 13/292,949, filed on Nov. 9, 2011, entitled "METHODS AND APPARATUS FOR SAG ADJUSTMENT", by Galasso et al., assigned to the assignee of the present application, which is incorporated herein by reference in its entirety.

The application with Ser. No. 13/292,949 claims the benefit of and claims priority of U.S. Provisional Patent Application Ser. No. 61/533,712, filed on Sep. 12, 2011, entitled "METHODS AND APPARATUS FOR SUSPENSION SET UP" by Galasso et al., assigned to the assignee of the present application, and is hereby incorporated by reference in its entirety herein.

This application is a continuation in part of and claims the benefit of co-pending U.S. patent application Ser. No. 13/022,346, filed on Feb. 7, 2011, entitled "METHODS AND APPARATUS FOR VIRTUAL SUSPENSION ADJUSTMENT", by Galasso et al., assigned to the assignee of the present application, which is incorporated herein by reference in its entirety.

The application with Ser. No. 13/022,346 is a continuation in part of and claims the benefit of co-pending U.S. patent application Ser. No. 12/727,915, filed on Mar. 19, 2010, entitled "METHODS AND APPARATUS FOR SELECTIVE SPRING PRE-LOAD ADJUSTMENT", by Cox et al., assigned to the assignee of the present application, which is incorporated herein by reference in its entirety.

The application with Ser. No. 13/022,346 claims the benefit of and claims priority of U.S. Provisional Patent Application Ser. No. 61/302,070, filed on Feb. 5, 2010, entitled "METHOD AND APPARATUS FOR SUSPENSION ADJUSTMENT" by Galasso et al., assigned to the assignee of the present application, and is hereby incorporated by reference in its entirety herein.

The application with Ser. No. 12/727,915 claims the benefit of and claims priority of U.S. Provisional Patent Application Ser. No. 61/161,552, filed on Mar. 19, 2009, entitled "METHODS AND APPARATUS FOR SELECTIVE SPRING PRE-LOAD ADJUSTMENT" by Cox et al., assigned to the assignee of the present application, and is hereby incorporated by reference in its entirety herein.

The application with Ser. No. 12/727,915 claims the benefit of and claims priority of U.S. Provisional Patent Application Ser. No. 61/161,620, filed on Mar. 19, 2009, entitled "METHODS AND APPARATUS FOR SELECTIVE SPRING PRE-LOAD ADJUSTMENT" by Cox et al., assigned to the assignee of the present application, and is hereby incorporated by reference in its entirety herein.

The application with Ser. No. 12/727,915 is a continuation in part of and claims the benefit of co-pending U.S. patent application Ser. No. 12/773,671, filed on May 4, 2010, entitled "SUSPENSION SYSTEM FOR A VEHICLE", by Galasso et al., assigned to the assignee of the present application, which is incorporated herein by reference in its entirety herein.

The application with Ser. No. 12/773,671 claims the benefit of and claims priority of U.S. Provisional Patent Application Ser. No. 61/175,422, filed on May 4, 2009, entitled "METHOD AND APPARATUS FOR VARIABLE DAMPING RATE" by Galasso et al., assigned to the assignee of the present application, and is hereby incorporated by reference in its entirety herein.

This application is a continuation in part of and claims the benefit of co-pending U.S. patent application Ser. No. 13/176,336, filed on Jul. 5, 2011, entitled "POSITIVE LOCK ADJUSTABLE SEAT POST", by Laird et al., assigned to the assignee of the present application, which is incorporated herein by reference in its entirety herein.

The application with Ser. No. 13/176,336 claims the benefit of and claims priority of U.S. Provisional Patent Application Ser. No. 61/361,376, filed on Jul. 2, 2010, entitled "POSITIVE LOCK ADJUSTABLE SEAT POST" by Laird et al., assigned to the assignee of the present application, and is hereby incorporated by reference in its entirety herein.

BACKGROUND

This invention relates to systems and methods for varying the height of a support on which a person may sit. More particularly, it is directed to a seat post for a bicycle that is adjustable while riding the bicycle.

When riding a bicycle, and in particular, the type of bicycle characterized as a "mountain bike", it is sometimes desirable to change the height of the seat with respect to the frame. For example, when descending steep hills, the rider many times prefers to sit lower on the bike or even to move his body further rearward such that he is positioned behind the saddle in an almost standing position. In these circumstances, it is useful to have a seat which may be adjusted into a lowered position such that the rider may sit lower or avoid having the saddle positioned at his chest level during the ride.

Conventionally, commercially available bicycles generally have height adjustable seats. When desiring a seat height change, the rider must stop and dismount from his bicycle in order to manually adjust the seat's height by adjusting a lever actuated seat post.

However, bicycle racers and others who desire an uninterrupted riding experience may find such starting and stopping of the bicycle in order to adjust the seats' height to be unproductive, inconvenient, and unpleasant. Thus, there is a need for a seat support for a bicycle whose height may be adjusted while the bicycle is being ridden.

The drawings referred to in this description should be understood as not being drawn to scale except if specifically noted.

BRIEF DESCRIPTION

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is applicable to alternative embodiments, modifications and equivalents, which may be included within the spirit and scope of the invention as defined by the appended claims.

Furthermore, in the following description of embodiments, numerous specific details are set forth in order to provide a thorough understanding of the present technology. However, the present technology may be practiced without these specific details. In other instances, well known methods, procedures, and components have not been described in detail as not to unnecessarily obscure aspects of the present disclosure.

Embodiments describe an adjustable seat post for a vehicle, the various height positions for which adjustments may occur are programmable by the rider. More particularly and as will be described herein, embodiments enable the regulation of fluid flow with a variable finite positioning seat post height mode in response to a movement of a motive source (any source of energy used to produce motion, e.g., solenoid) attached to the seat post. As such, at least two possible position modes of an adjustable seat post are, but not limited to, the following: (1) an infinite position mode; and (2) a finite position mode. Further, the seat post's movement to the intended position is accomplished, in embodiments, such that the seat post arrives at the desired position in a gentle manner and without overshoot.

The following discussion will first describe conventional seat posts and limitations thereof. The discussion then turns to embodiments: the structure and function of the vehicle assembly along with a seat post and a user interface attached thereto (e.g., a lever, set of levers, mobile device, power meter, heart rate monitor, voice activation, GPS device with stored map); a bushing configured for remedying at least a majority of the "play" between the upper and lower post of the seat post; and an electromechanical controller configured for adjusting a seat post according to location, terrain detail, and/or physiological human factors.

Figure 1:
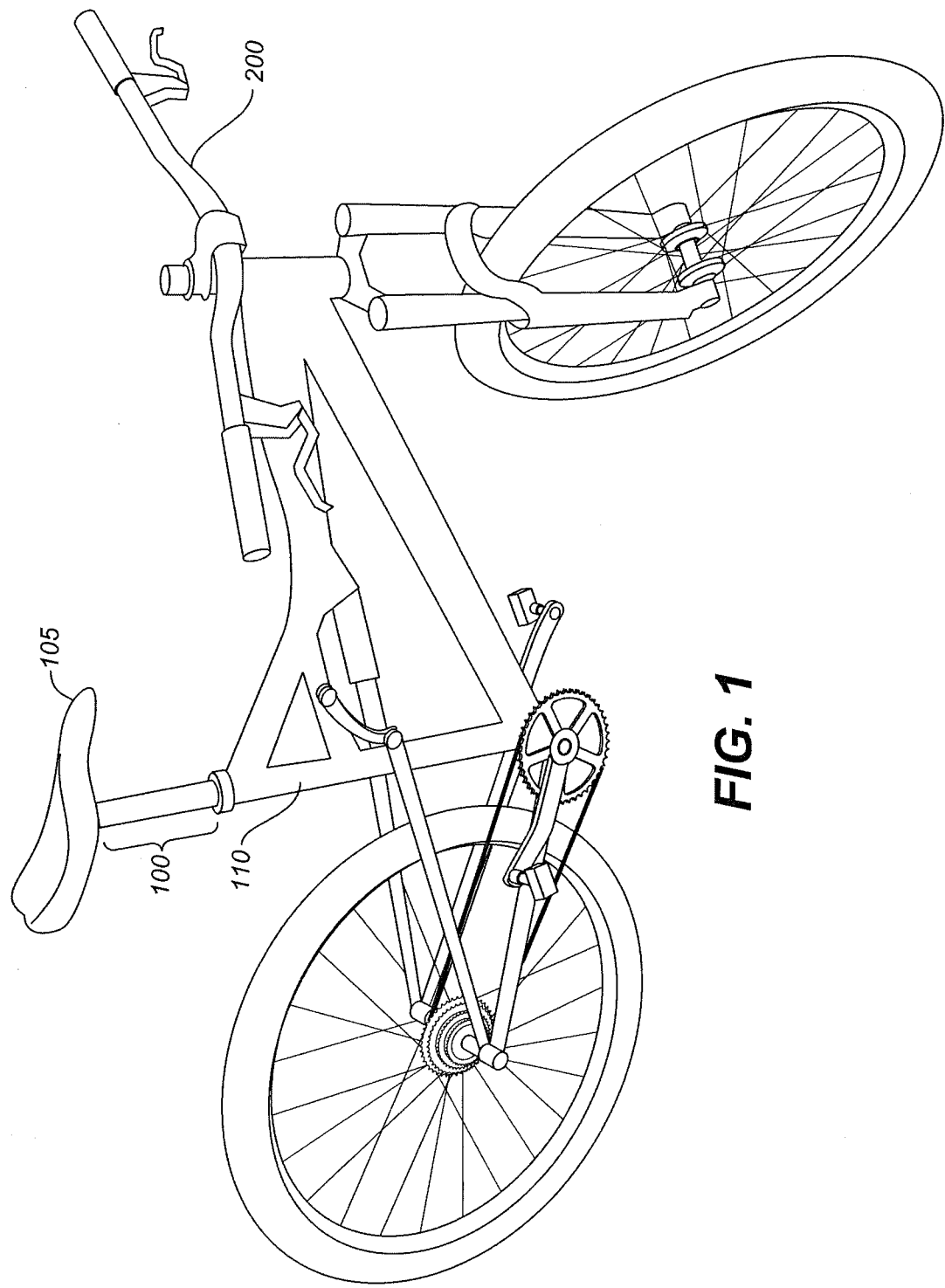
FIG. 1 depicts a perspective view of a conventional seat post attached to the saddle and the bicycle frame.

Referring now to FIG. 1, a bicycle seat post 100 is a tube that extends upwards from the bicycle frame 110 to the saddle 105 (bicycle seat). The amount that the seat post extends out of the frame can usually be adjusted. Seat posts may be made of various materials, such as, but not limited to being, the following: steel, aluminum, titanium, carbon fiber, and aluminum wrapped in carbon fiber. Seat posts generally clamp onto saddle rails. Generally, old or inexpensive seat posts slide into a separate clamp that then itself clamps to the saddle rail.

Various types of seat posts may include at least one or more of the following types: plain; micro-adjustable; integrated; aero; suspension; pivotal; seatmast and cap; and dropper. The plain seat post tends to be found on older or less expensive bikes or kids' bikes, and consists of a tube which may decrease in diameter for about the last inch on the lower end while having a separate clamping mechanism at the upper end.

In contrast to the "plain" seat post, the dropper seat post, which generally appears on mountain bikes, can be remotely shortened (lowered) using a control lever positioned on the bicycle's handlebar. On technical sections of a trail, a rider may cause the seat post to lower by triggering the actuating lever on the handlebar while the rider also depresses the saddle. Typically, the actuating lever of a dropper seat post will open a valve or latch in the seat post so that the seat post can move up or down. Dropper seat posts have an air spring and use the rider's weight to move them down, and will only raise themselves when the valve or latch internal to the seat post is opened (via handlebar remote). Conventional dropper seat posts are "micro-adjustable". There are two types of microadjustable seat posts: (1) seat posts that can be continuously adjusted to an infinite number of positions; and (2) seat posts that can only be adjusted to a predetermined (preprogrammed) number of positions.

For example, with regard to seat posts that can only be adjusted to a preprogrammed number of positions, the seat post adjustment positions may be that of the following three positions: up; middle; and down. Generally, the rider prefers that the seat post be in the "up" position during a ride over flat terrain, a road surface, or pedaling up small hills on a road surface. The rider generally prefers that the seat post be in the "middle" position when the rider still wants a small amount of power through pedaling but yet would still like the saddle to be at least partially out of the way. This situation may occur while riding down a gentle hill or when the rider anticipates having to climb a hill immediately after a short decent. The rider generally prefers that the seat post be in the "down" position when the rider is descending a steep hillside. In this situation, the rider would be positioned rearward of the saddle and essentially be in a mostly standing position. By doing such, the rider changes his center of gravity to be rearward of the bicycle and lower, thereby accomplishing a more stable and safer riding position. Additionally, since the saddle is lowered, it is not positioned in the riders' chest area, contributing to a safer ride.

Some mountain bikers prefer that the infinitely adjustable seat post be installed on their mountain bikes, enabling them to adjust their saddle at any given moment to any given terrain detail.

As opposed to the infinitely-adjustable seat post that can require hunting and pecking to find a desirable position between "full-up" and "full-down" positions, other mountain bikers prefer that the dropper seat post has three predetermined positions (or any other finite number of positions) be installed on their mountain bikes, which the riders grow accustomed to through use: the full-up position; the full-down position; and the middle position. The full-up and full-down positions are essentially the same whether it is a three-position seat post or an infinitely-adjustable seat post, as they have mechanical stops.

While the conventional dropper seat post enables a faster and more enjoyable ride, there are also certain inconveniences for the bicycle rider that accompany its use. For example, once the seat post is user actuated through the remote handlebar lever, the seat post generally arrives at least slightly later to its intended position than that arrival timing desired by the rider. There is a lag time between the rider's instruction to go to a different position and the actual arrival of the seat post to that position. This lag time provides for a more complicated and difficult riding condition, especially for racers. Additionally, and conversely, other conventional dropper seat posts arrive at the intended position with too much aplomb, causing a vibration and jerk which is uncomfortable and distracting to the rider. This hard and abrupt arrival also may cause the seat post to overshoot the intended position.

Another inconvenience provided by the conventional dropper seat post involves the gap existing between the seat post and the tube (lower post) within which the seat post telescopically slides. There is "play" between the seat post and the lower post. This play causes the seat post, and hence the saddle, to rotate about the seat post axis slightly during the ride in an impromptu fashion. This causes a vague feedback sensation while riding and a distraction.

Embodiments provide for a dropper seat post which is capable of accomplishing both of the foregoing modalities: (1) user-programmability to accommodate a definitive (finite) number of seat post positions (e.g., up, middle, and down); (2) user-programmability to set the height of the definitive (finite) positions; and (3) user-programmability to accommodate an infinite number of positions. As will be described herein, a variety of mechanisms enable the user interface actuated seat post to switch/rotate between these modalities via buttons, switches, levers, etc. As will be further described below, the instructions received via the user interface (e.g., handlebar lever) cause components (e.g., valves, cam) positioned within the seat post to shift/rotate, thereby controlling fluid flow there through and, ultimately, the vertical movement of the seat post and the saddle.

Embodiments provide a mechanism which enables a proportional movement and the gentle arrival of the seat post to various intended positions, based upon the calculated position of the seat post itself during movement. An electrical system, as will be described herein, is used to control the movement of the seat post. The electrical system senses the position of the seat post relative to its intended position, and sends signals that actuate components (e.g., cam, valves) within the seat post. These components, as will be described herein, cause the seat post to slow down as the seat post starts getting closer to the intended position, thereby creating a gentle arrival for the seat post.

Embodiments provide a mechanism for preventing the majority, if not all, of the movement between the seat post and the lower post through the use of a novel bushing design providing anti-rotation capabilities. As will be described in greater detail below, in one embodiment, the bushing is split, enabling a preload capability that functions to more securely retain the upper and lower posts of the seat post in a stable position during the ride.

In one embodiment, the seat post is actuated by a controller designed for receiving and analyzing input associated with a cyclist's heart rate as well as the cyclist's GPS coordinates. For example, if the controller receives input that describes the cyclist's heart rate as being lower than a given preprogrammed threshold while riding, then the controller may signal to the seat post to move up or down, causing the cyclist's work rate and heart rate to increase or decrease. In another example, if the controller receives input that describes the cyclist's GPS coordinates as being such that the cyclist is just about to arrive at terrain having a steep descent, the controller may cause the seat post to lower in preparation for the descent.

While the examples herein may often be described in reference to bicycles, the elements disclosed herein are suitable for use on a wide variety of vehicles.

Figure 2:
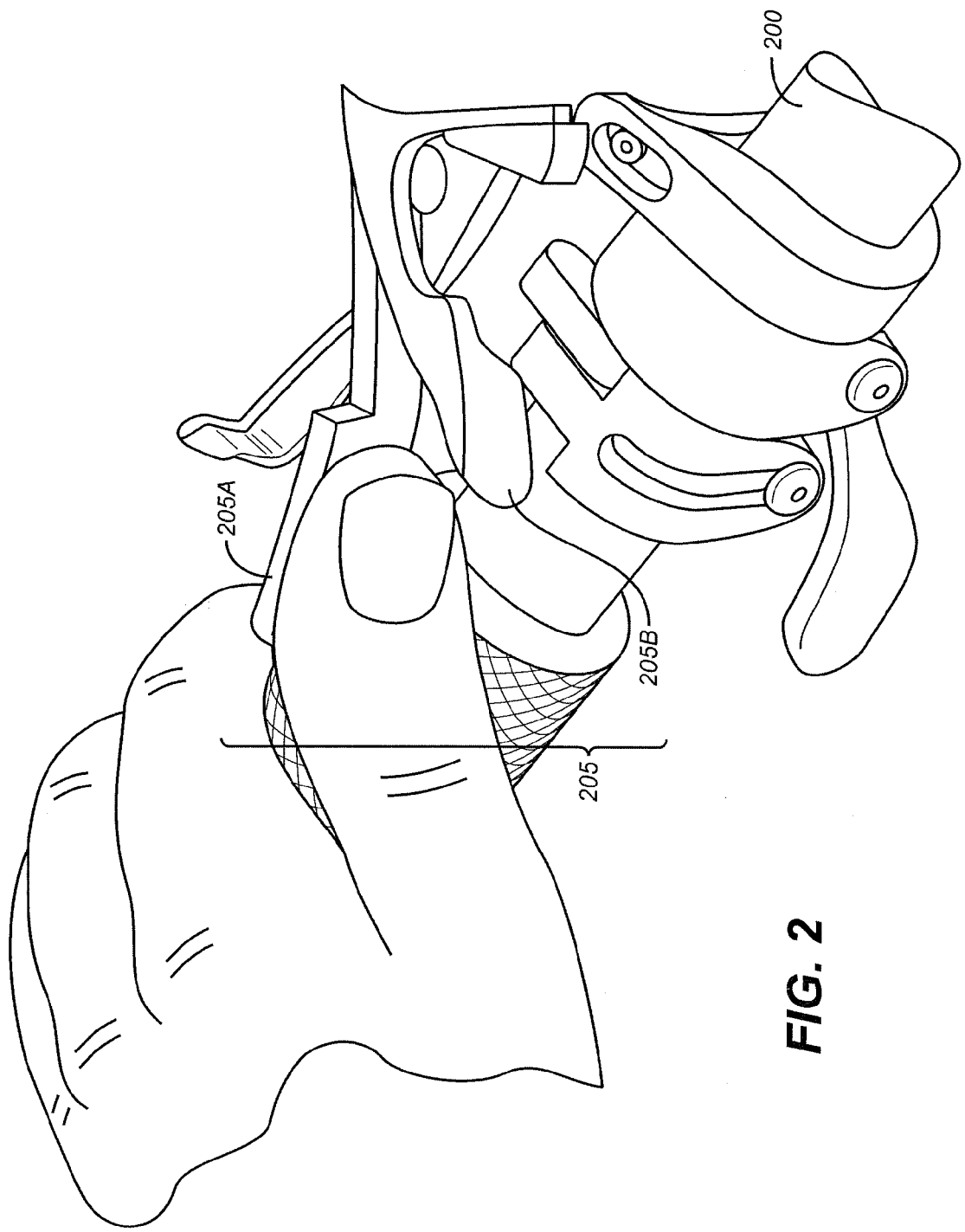
FIG. 2 depicts a perspective view of a handle bar coupled with a set of control levers, in accordance with an embodiment.

FIG. 2 depicts a handle bar 200 with a set of control levers 205 coupled therewith, according to an embodiment. The set of control levers 205 is a type of user interface with which the user employs for communicating seat post height instructions to the seat post. Of note, the set of control levers 205 is used herein to describe various embodiments. However, it should be understood that the term, "user interface" may be substituted for the set of control levers 205, in various embodiments. It should also be appreciated that the user interface may be at least, but not limited to, any of the following components capable of communicating with the seat post: wireless device, power meter, heart rate monitor, voice activation device, GPS device having stored map, graphical user interface, button, dial, smart phone (e.g., iPhone™), and lever)

The set of control levers 205 includes at least one control lever, such as the first control lever 205A and the second control lever 205B. The set of control levers 205 are mechanically and/or electronically connected (via wire/cable and/or wirelessly) to various components within the seat post. When the cyclist moves the set of control levers 205, via the connections between the set of control levers 205 and the seat post, he is causing a cam within the seat post to shift positions. The shifting cam, in turn, moves against valves, causing the valves within a valve system to open and/or close. This opening and/or closing of the valves control the fluid movement through and surrounding the valve system.

Figure 3A:
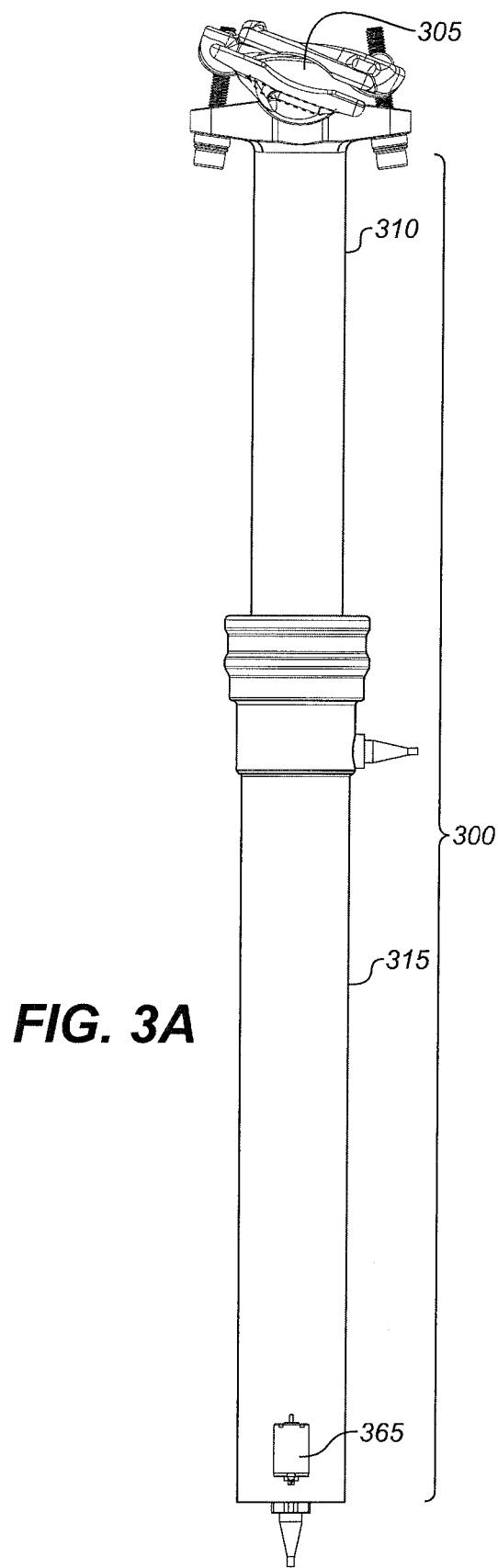
FIG. 3A depicts a perspective view of a seat post coupled with a saddle clamp assembly, in accordance with an embodiment.

FIG. 3A depicts a perspective view of a seat post 300 coupled with a saddle clamp assembly 305. In one embodiment, the seat post 300 includes an upper post 310 and a lower post 315 within which the upper post 310 telescopically slides upon actuation of a handle bar lever, such as the set of control levers 205 shown in FIG. 2.

Figure 3B:
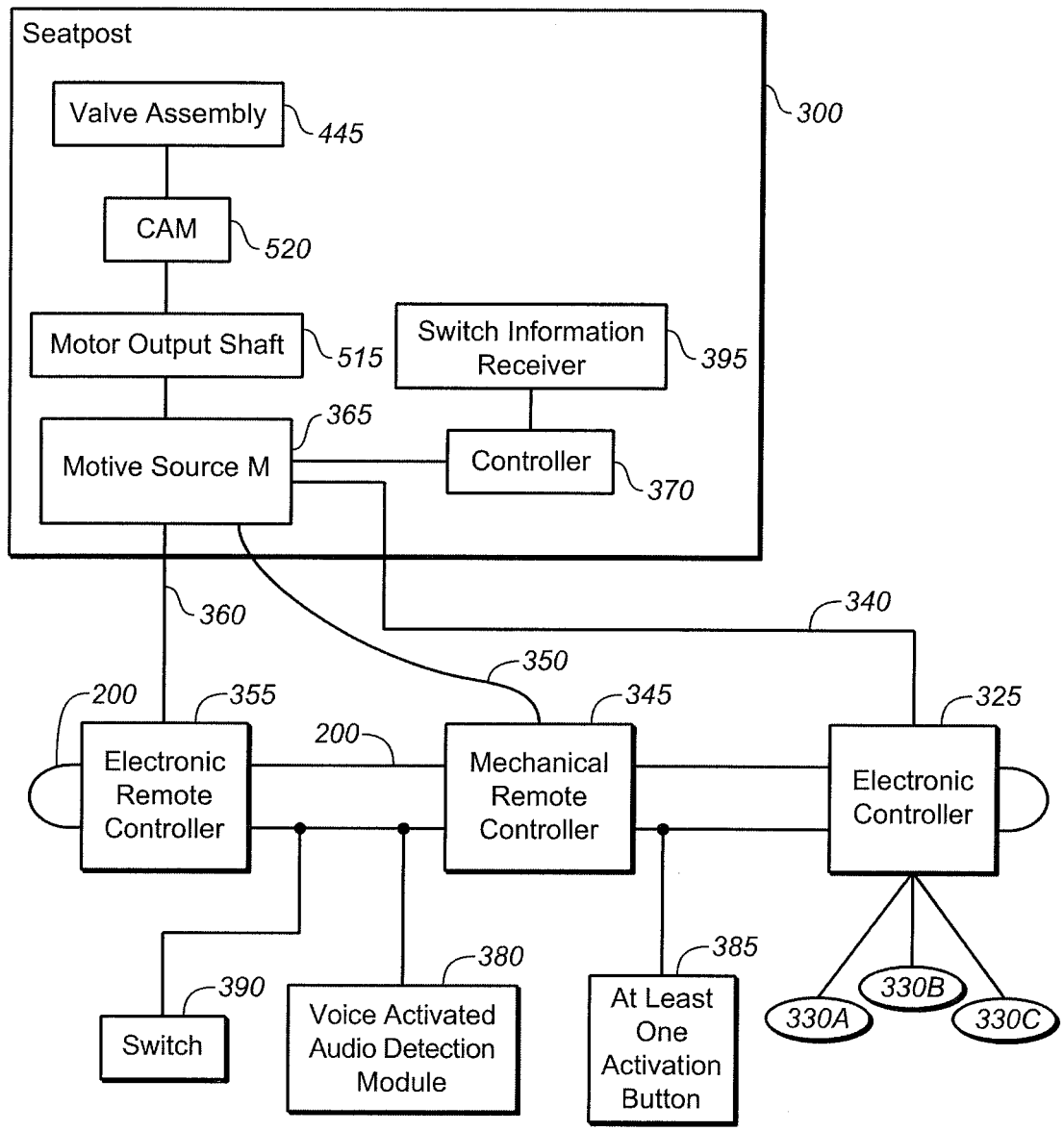
FIG. 3B depicts a high-level block diagram schematically depicting a method for adjusting a valve assembly such that the seat post is enabled to move into different positions, in accordance with an embodiment.

FIG. 3B depicts a high-level block diagram schematically depicting a method for adjusting the valve assembly 445 such that the seat post 300 is enabled to move into different positions, in accordance with an embodiment. As shown in FIG. 3B, the externally positioned electronic remote controller 355 or electronic controller 325 may be positioned anywhere. For example, when the system as described herein is associated with a bicycle, the electronic remote controller 355 or the electronic controller 325 may be mounted on the handlebar 200. The handlebar 200, or any other component of a bicycle, may variously contain one or more of the following attached thereto: an electronic controller 325; a mechanical remote controller 345; and an electronic remote controller 355.

As shown in FIG. 3B, a motive source M 365 is associated with the cam 520. The motive source M 365 can comprise any conventional source of torque, including servo-motors and/or mechanical gear drives (neither shown). The motive source M 365 may be associated with a controller, for example: (a) an electrical wire 360 for connecting motive source M 365 to an externally positioned electronic remote controller 355; (b) a mechanical cable 350 for connecting motive source M 365 to an externally positioned mechanical remote controller 345; and (c) an electronic controller 325, such as a CPU, receives control signals from one or more sensors 330A-C and sends control signals to the motive source M 365. Sensors 330A-C may detect such example conditions as vertical acceleration, speed, and inclination. Additionally, the motive source M 365 may also have a controller 370 therein capable of receiving instructions from the electronic remote controller 355 and the electronic controller 325, and translating these instructions into movement of components attached thereto. The controller 370 may also be configured to function as the electronic controller 325 described herein.

In general, and as will be described herein in greater detail, in one embodiment the rider is able to cause the seat post 300 to move up and/or down by moving a lever of a remote controller (either the electronic remote controller 355 and/or the mechanical remote controller 345) attached to the handlebar 200. The remote controller receives the seat post height instructions from the rider, and sends these instructions through either the electrical wire 360 and/or the mechanical cable 350 to the motive source M 365. The controller 370 of the motive source M 365 then translates these instructions into particularized movement of the motor output shaft 515. As will be described herein, the motor output shaft 515 is attached to the cam 520 and moves/rotates in response to the movement of the motor output shaft 515. The rotation of the cam 520 variously serves to seat and unseat check valve balls of the check valves (of the valve assembly 445), thereby causing the check valves to open and/or close. Generally, the operation of a cam in relation to check valves is known in the art, a discussion of which may be found in, "Gas Spring Curve control in an Adjustable-Volume Gas-Pressurized Device", by Robert C. Fox, U.S. Patent Publication No. 2008/0116622, all of which is incorporated in its entirety herein. As will also be described herein, the opening and closing of the check valves has a direction relationship with the compression and extension of the seat post 300. Thus, the remote controllers attached to the handlebar 200 ultimately control the opening and closing of the check valves of the valve assembly 445, and hence the extension and compression of the seat post 300.

Shown and as will be described herein, in one embodiment, the check valves of the valve assembly 445 are arranged in a rotary cam layout. In one embodiment, the check valves of the valve assembly 445 are arranged inline with each other. This inline arrangement enables a linear cam to displace the valve balls of the check valves. In another embodiment, the check valves of the valve assembly 445 are arranged in series and opposed to each other such that the opening of each check valve of the check valves, one at a time, results in a one-way flow.

Figure 4:
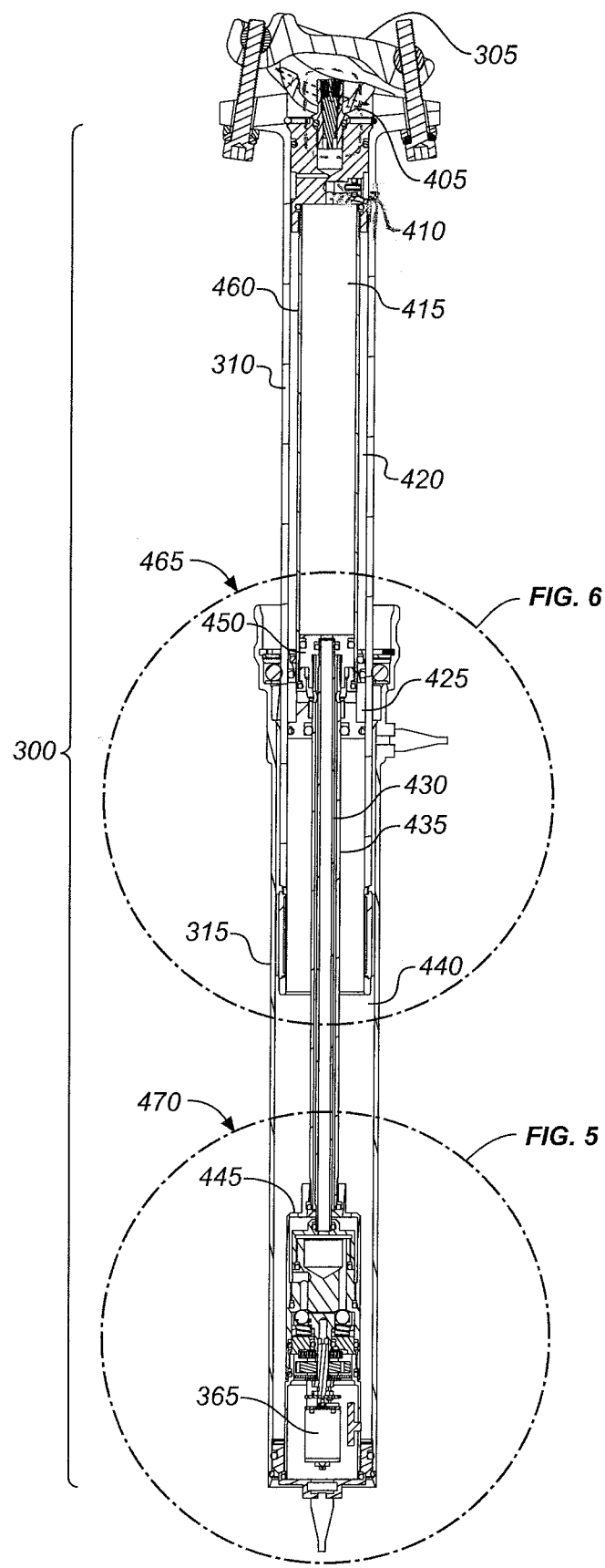
FIG. 4 depicts a sectional view of a seat post, in accordance with an embodiment.

FIG. 4 depicts a sectional view of the seat post 300 of FIG. 3A, shown in an extended position, in accordance with an embodiment. As was described herein, the seat post 300 in FIG. 3A depicts the upper post 310 coupled with the saddle clamp assembly 305 and is partially positioned within the lower post 315 such that the upper post 310 is able to telescopically slide in and out of the lower post 315. Referring once again to FIG. 4, at the upper end of the seat post 300 is depicted a pressurized gas fill valve 405 and an oil fill valve 410. Internal to the upper post 310 is the main oil chamber 415, the inner tube one 460, the pressurized air chamber 420 (above the internal floating piston 620), and the outer tube one 310, which is shown integral to the upper post. At the upper end of the lower post 315 is shown the piston 450 and the accumulator oil chamber 425 (below the internal floating piston 620). Internal to the lower post 315 is depicted the inner tube two 430, the outer tube two 435, a sealed, unpressurized air chamber 440 containing unpressurized air, and the valve assembly 445 along with the motive source M 365 (from FIG. 3A and FIG. 3B). (With regard to the unpressurized air chamber 440, its presence is not necessary for embodiments to function. However, in one embodiment, the pressure, in the unpressurized air chamber 440, is used to activate a pressure sensor 570 [of FIG. 5] which may be used as the displacement sensor. In one embodiment, the displacement sensor is the pressure sensor 570. The pressure sensor 570, in various embodiments, measures pressure in the unpressurized air chamber 440 in the lower post 315 and/or the accumulator oil chamber 425 and/or the pressurized air chamber, 420.)

The detail 465 (including the piston 450) and the detail 470 (including the valve assembly 445) will be described in greater detail below.

Figure 5:
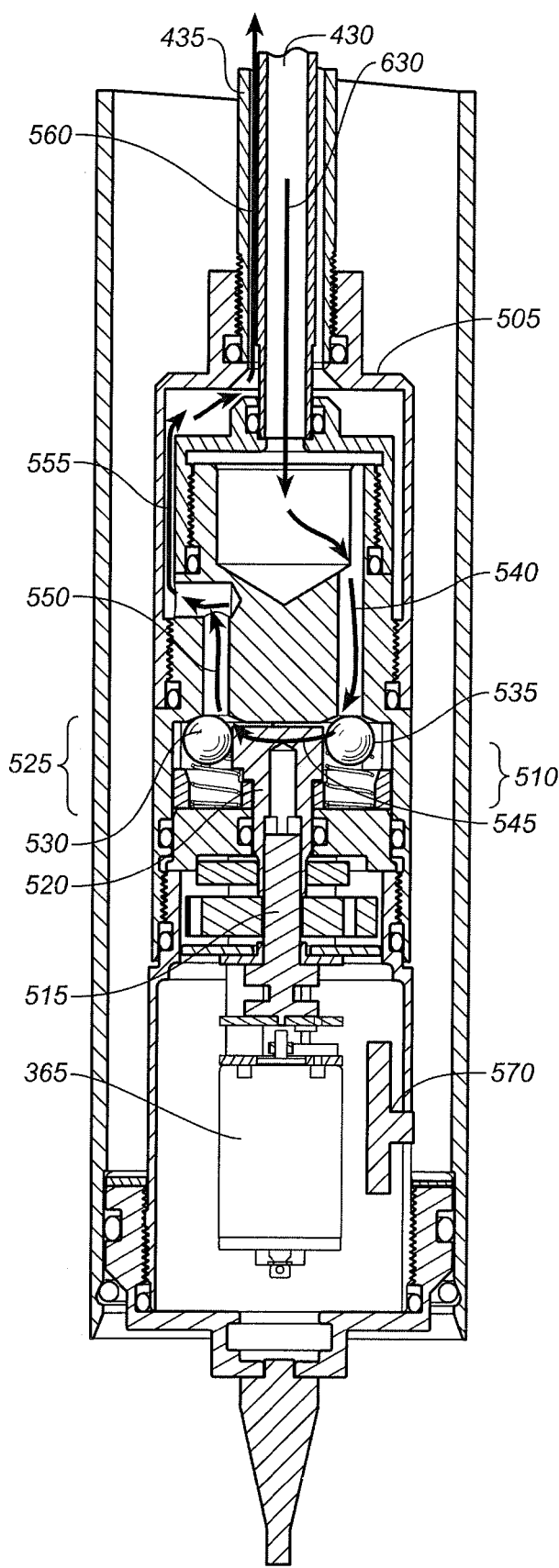
FIG. 5 depicts a sectional view of a portion of FIG. 4, showing flowpath arrows describing a flowpath during compression of the seat post, in accordance with an embodiment.
Figure 6:
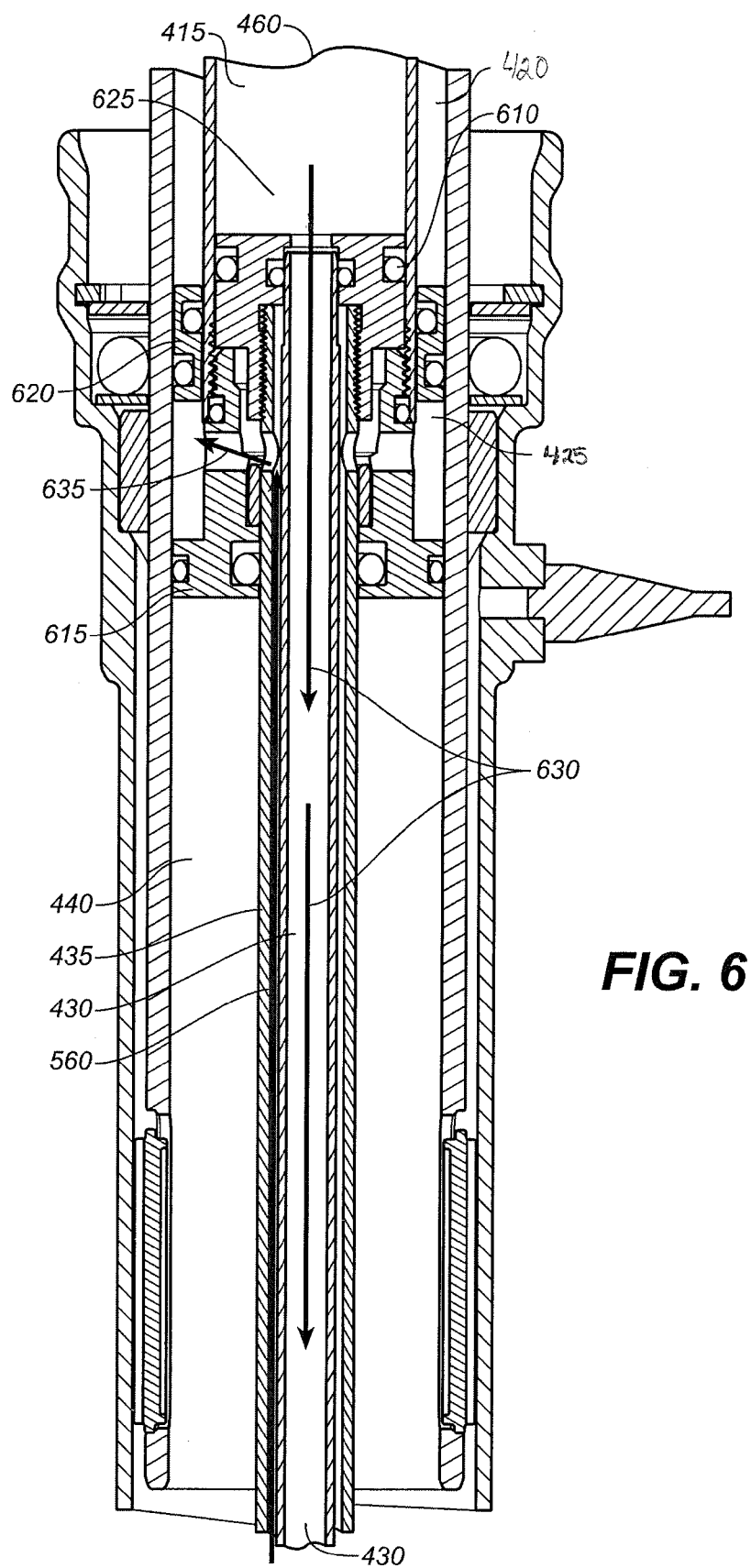
FIG. 6 depicts a sectional view of a portion of FIG. 4, showing flowpath arrows describing a flowpath during compression of the seat post, in accordance with an embodiment.

Next, with reference to FIG. 5 and FIG. 6, the operation, while in the compression setting, of various components within the seat post 300 and the fluid flowpath will be described. FIG. 5 depicts a sectional view of the detail 470 of FIG. 4, including the valve assembly 445, in accordance with an embodiment. FIG. 6 depicts a sectional view of the detail 465 of FIG. 4, in accordance with an embodiment. As will be seen, the four check balls (check valve ball set one 535 [containing two check balls] and check valve ball set two 530 [containing two check balls]) interact with the cam 520 to provide four different settings of the valve assembly 445: (1) all check valves are held open (enabling both compression and extension of the seat post 300); (2) all check valves are closed (neither compression nor extension of the seat post 300 may occur); (3) the check valve ball set one 535 is held open while the check valve ball set two 530 is not held open by the cam 520 (enabling the extension of the seat post 300 while preventing compression of the seat post 300); and (4) the check valve ball set two 530 is held open while check valve ball set one 535 is not held open by the cam 520 (enabling the compression of the seat post 300 while preventing extension of the seat post 300).

With reference still to FIG. 5 and FIG. 6, in one embodiment, the rider manipulates the set of control levers 205 that are positioned on the handlebar 200 of the bicycle to achieve the "compression setting". In various embodiments, the set of control levers 205 includes any form of lever or button that may at least be rider-activated to cause the cam 520 to shift/rotate to a different position. The set of control levers 205 may be at least one actuatable (able to be actuated) trigger (the actuating of the trigger causes the instructions to be sent to the motive source M 365) that is configured for receiving a pattern of touches. The pattern of touches represents a seat post height position instruction. The seat post height position instruction includes, among other instructions, the following: an infinite positioning seat post height mode (no set number of positions preprogrammed into the controller 370 coupled to the motive source M 365); and a finite positioning seat post height mode (e.g., three positions: up; middle; and down). The set of control levers 205 are attached to the motive source M 365 via a wire and/or wireless capability. Of note, the user interface, in one embodiment, is attached to the motive source M 365 via a wire and/or wireless capability. The set of control levers 205 is but a type of user interface with which the user may interact. The motive source M 365 is coupled to the motor output shaft 515, which is itself coupled to the cam 520. Additionally, the controller 370 may be preprogrammed to include a set position, such as a "middle position". The set of control levers 205, in various embodiments, includes at least one activation button 385 coupled to the handlebar 200. The at least one activation button 385 activates a pre-programmed position for the seat post 300, wherein the programming of the pre-programmed position for the seat post 300 was performed by the manufacturer, rider, and/or some other entity. In one embodiment, for example, the pre-programmed position may be that of the middle position. However, it should be understood that the pre-programmed position may be any number and location of positions. For instance, the up and down positions may be preprogrammed to be anywhere between the mechanical hard stops (at full-up and full-down positions). Thus, the user is able to reprogram the positions (the positions having already been previously programmed) of the seat post 300 with the user's desired positions.

In response to the compression setting instruction from the rider via the set of control levers 205, the motive source M 365 is instructed to cause the motor output shaft 515 to rotate, thereby also causing the cam 520 that is attached to the motor output shaft 515 to also rotate. The rotation of the cam 520, according to compression setting instructions (via the set of control levers 205), unseats the check valve ball set two 530 (Check valve ball set two 530 includes two check valve balls spaced 180 degrees apart from each other, in one embodiment. Of note, the check valve ball set one 535 is spaced apart about 60 degrees apart from the check valve ball set two 530. The two check valve balls of check valve ball set one 535 are spaced about 180 degrees apart from each other) of the check valve two 525. The cam 520 displaces check valve ball set two 530 to allow for fluid to flow through the check valve two 525 and to allow for the compression of the seat post 300 (the movement of the upper post 310 into the lower post 315 after the rider sits on the saddle, as will be described below), which means that the oil is enabled to flow from the main oil chamber 415 to the accumulator oil chamber 425 through the check valve two 525 which has the displaced check valve ball set two 530.

When the rider initially sits on the bicycle saddle, the pressure in the main oil chamber 415 (see FIG. 4 and FIG. 6) is increased. This pressure increase in the main oil chamber 415 easily displaces check valve ball set one 535. If the check valve two 525 is open (due to rotation of the cam 520 unseating the check valve ball set two 530), then the upper post 310 of the seat post 300 is enabled to slide further into the lower post 315. Thus, the check valve one 510 and the check valve two 525 are open during the compression setting and after the rider initially sits on the saddle, allowing fluid to flow there through.

Figure 7A:
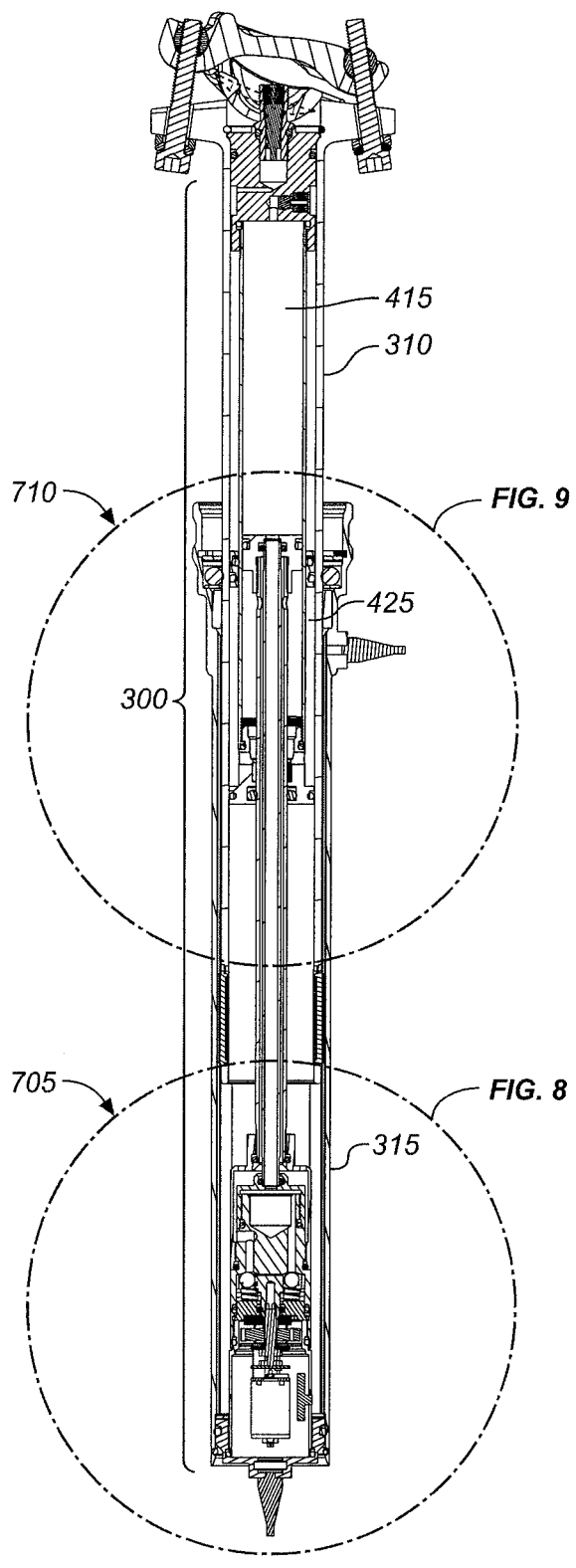
FIG. 7A and FIG. 7B depict a sectional view of a seat post during compression states, in accordance with an embodiment.
Figure 7B:
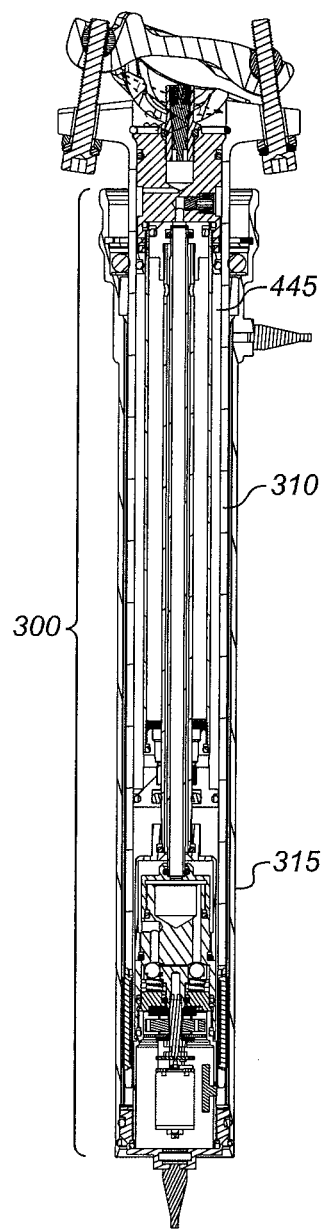

The arrows in both FIG. 5 and FIG. 6 show the direction of and the fluid flowpath while the check valves are positioned for the compression setting. FIGS. 7A and 7B depict a sectional view of the seat post 300 during compression states, in accordance with an embodiment. The detail 705 and the detail 710 will be described in greater detail below with reference to FIG. 8 and FIG. 9.

For example, with reference to FIG. 7A, when the upper post 310 slides further into the lower post 315, the main oil chamber 415 holding fluid decreases in size; pressure is placed on the fluid within the main oil chamber 415, causing the fluid to flow out of (see flowpath arrow 630 of FIG. 6) the main oil chamber 415 and into the inner tube two 430 positioned within the lower post 315. As can be seen in FIG. 7B, during the compression setting, the upper post 310 has slid entirely into the lower post 315. As a result, substantially all (all of at least most of the fluid) of the fluid within the main oil chamber 415 has entered and exited the inner tube two 430. Thus, while the rider continues to sit and thereby exert downward force on the saddle and the seat post 300, the increased pressure in the main oil chamber 415 causes the fluid to flow from the inner tube one 460 that houses main oil chamber 415 into the inner tube two 430. The center 625 (see FIG. 6) of the piston 450 is open and allows flow from the inner tube one 460 to the inner tube two 430.

The fluid flows through the inner tube two 430 and to and through (see flowpath arrows 540, 545, and 550) the open check valve one 510 and the open check valve two 525. After flowing through the open check valve two 525, the fluid flows (see flowpath arrow 555) through the outer valve coupler 505 and into the outer tube two 435 (see flowpath arrow 560). From the outer valve coupler 505, the fluid flows into the accumulator oil chamber 425 (see flowpath arrow 635 of FIG. 6). As can be seen in FIG. 7A and FIG. 7B, some fluid flows into the accumulator oil chamber 425 during the sliding of the upper post 310 into the lower post 315 during compression. Some fluid also flows between outer tube two 435 and inner tube one 460 during compression. Thus, the volume of fluid that enters the accumulator oil chamber 425 is equal to the full volume of outer tube two 435 (as if it were solid) that enters the inner tube one through the seal head 615 (of FIG. 6).

FIG. 6 also depicts a sealhead 615, a pressurized air chamber 420, an unpressurized air chamber 440, a main oil seal 610, and an internal floating piston 620. Of note, during the compression of the seat post 300, the internal floating piston 620 is displaced upward. This upward displacement increases the pressure in the pressurized air chamber 420.

As the seat post 300 approaches the intended position as was instructed by the rider via the set of control levers 205, the motive source M 365, being coupled with an electrical computer system, is preprogrammed to cause the motor output shaft 515 to rotate the cam 520 into a position such that the check valve ball set one 535 is once again seated within the check valve one 510. As will be described herein in more detail in regards to two PID loops integrated within embodiments, the controller 370 is constantly checking the current position of the seat post 300 in relation to the desired position (in a first PID loop). At a certain point, the valve assembly 445 starts to close, which slows the movement of the seat post 300. As the seat post 300 approaches the desired position, the valve assembly 445 is adjusting itself to regulate the speed of the seat post 300. Moreover, there is another PID loop (separate from the "first" PID loop) for the valve assembly 445 that constantly monitors the position of the cam 520 (guided by the motive source M 365) vs. the set point of the cam 520. Thus, the motor (motive source M 365) can slow itself down (in addition to slowing the seat post 300 down by gradually closing the valve assembly 445 before it reaches the motor setpoint so that the cam 520 won't overshoot its intended position. As will also be described herein in more detail, this is a gradual process that allows control of the return speed of the seat post 300, prevents over-shoot of the seat post 300, and allows adjustment even after the valve assembly 445 is in a closed position. Since fluid may no longer flow through the check valve one 510 due to its being in a closed position, the compression movement of the seat post 300 is halted.

Of significance, in various embodiments, the check valves, check valve 510 and check valve 525, of the valve assembly 445, are positioned in a series, relative to each other, and opposed to each other. This particular positioning enables one-way only movement. For example, the seat post 300 may only extend or only compress in response to a movement of the motive source M 365.

Figure 8:
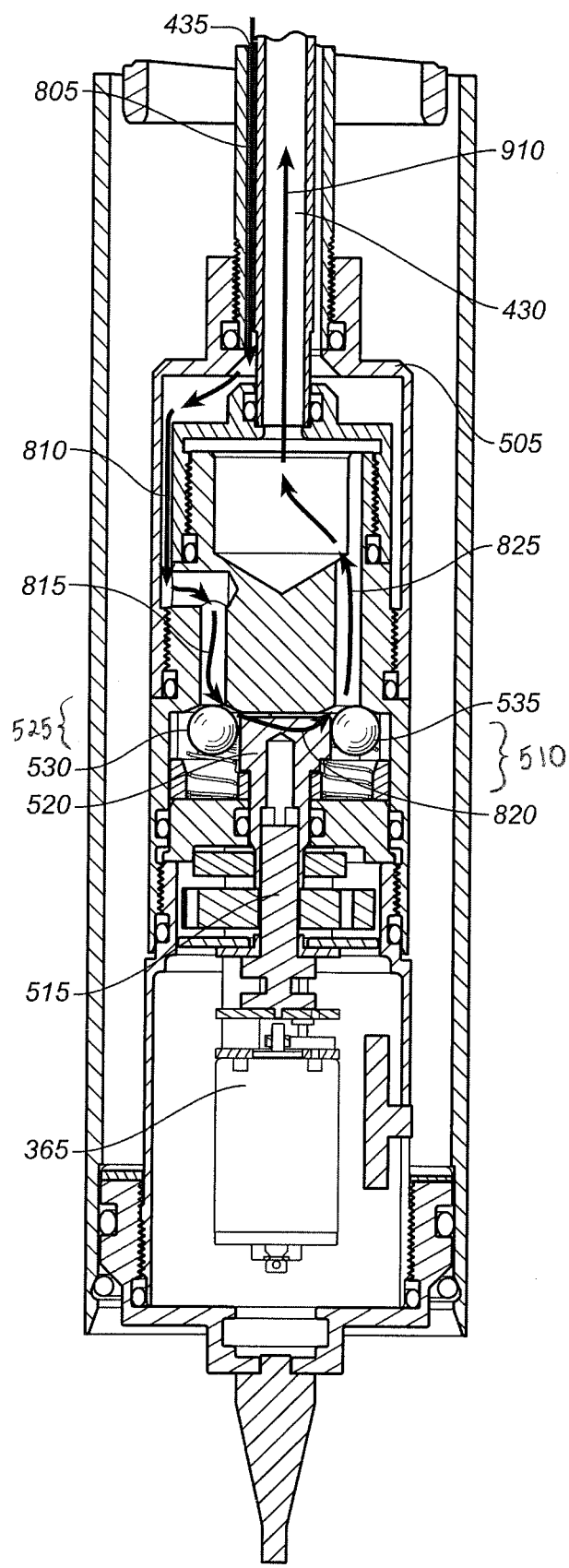
FIG. 8 depicts a sectional view of FIG. 4, showing flowpath arrows describing a flowpath during extension of the seat post. This actually shows the compression phase, in regards to the valves, not extension. Arrows should be reversed, or I should supply another figure.
Figure 9:
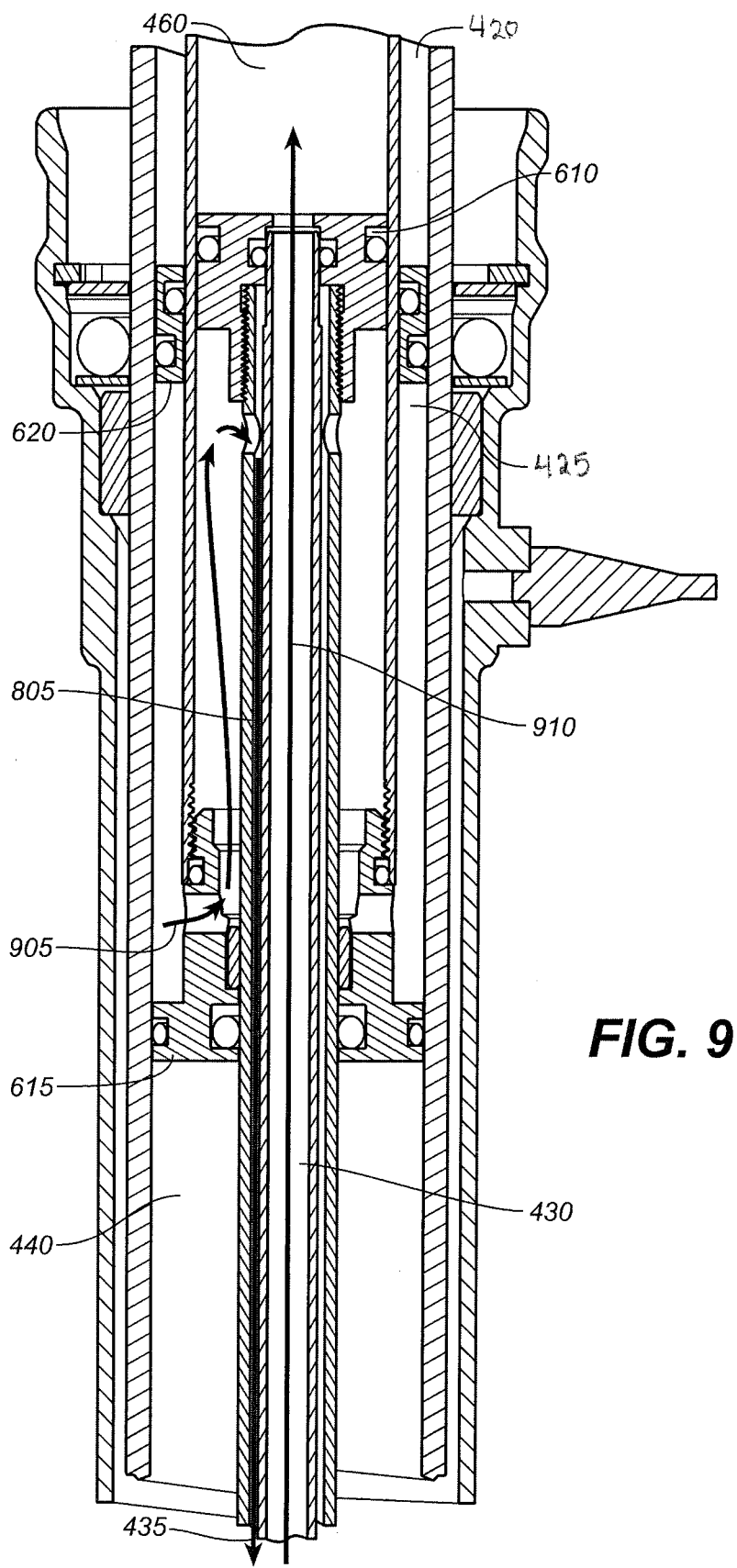
FIG. 9 depicts a sectional view of FIG. 4, showing flowpath arrows describing a flowpath during extension of the seat post.

FIG. 8 and FIG. 9 depict a sectional view of FIG. 4, showing flowpath arrows describing a flowpath during an extension of the seat post 300, in accordance with an embodiment. FIG. 8 depicts a sectional view of the detail 705 of FIG. 7A, in accordance with an embodiment. FIG. 9 depicts a sectional view of detail 710 of FIG. 7A, in accordance with an embodiment. The flowpath arrows describing the flowpath during an extension of the seat post 300 appear in a reversed state as those flowpath arrows describing the flowpath of fluid during the compression of the seat post 300.

In one embodiment, the rider manipulates the set of control levers 205 to achieve an "extension setting". In response to the extension setting instruction from the rider via the set of control levers 205, the motive source M 365 is instructed to cause the motor output shaft 515 to rotate, thereby also causing the cam 520 to rotate. The rotation of the cam 520, according to the extension setting instructions (via the set of control levers 205), unseats check valve ball set one 535 of the check valve one 510, thereby opening up the check valve one 510, to assist in allowing the fluid from the accumulator oil chamber 425 to eventually flow there through and arrive at the main oil chamber 415.

More specifically, and with reference to FIG. 8 and FIG. 9, the fluid flowpath may be described as follows with reference to an extension setting, in accordance with an embodiment. Once the rotation of the cam 520 causes the check valve one 510 to open by way of unseating check valve ball set one 535, the fluid residing in the accumulator oil chamber 425 begins to flow toward and through (see flowpath arrow 905 and 805) the outer tube two 435.

The fluid then flows through (see flowpath arrow 810) the outer valve coupler 505 and toward (see flowpath arrow 815) the check valve two 525. The fluid flow from the outer valve coupler 505 pushes the check valve two 525 downward into its seat proportional to the pressure from the fluid moving toward the check valve two 525 from the accumulator oil chamber 425.

The fluid continues to flow (see flowpath arrow 820) from the opened check valve two 525 toward and through the opened check valve one 510. The fluid then flows from the opened check valve one 510 into and through (see flowpath arrow 825) inner tube two 430. From the inner tube two 430, the fluid flows (see flowpath arrow 910) into the main oil chamber 415.

Of significance, the flow of the fluid as described herein is part of a gradual process obtained through the use of the two PID loops.

Once an intended extension position is reached, the cam 520 rotates, prompted by the motive source M 365, such that the cam 520 knocks the check valve ball set one 535 back onto its seat. The fluid flow through the check valve one 510 is then halted.

Next will be described, with reference to FIGS. 10-13, the check ball valves of the check valves in the four various position settings.

Figure 10:
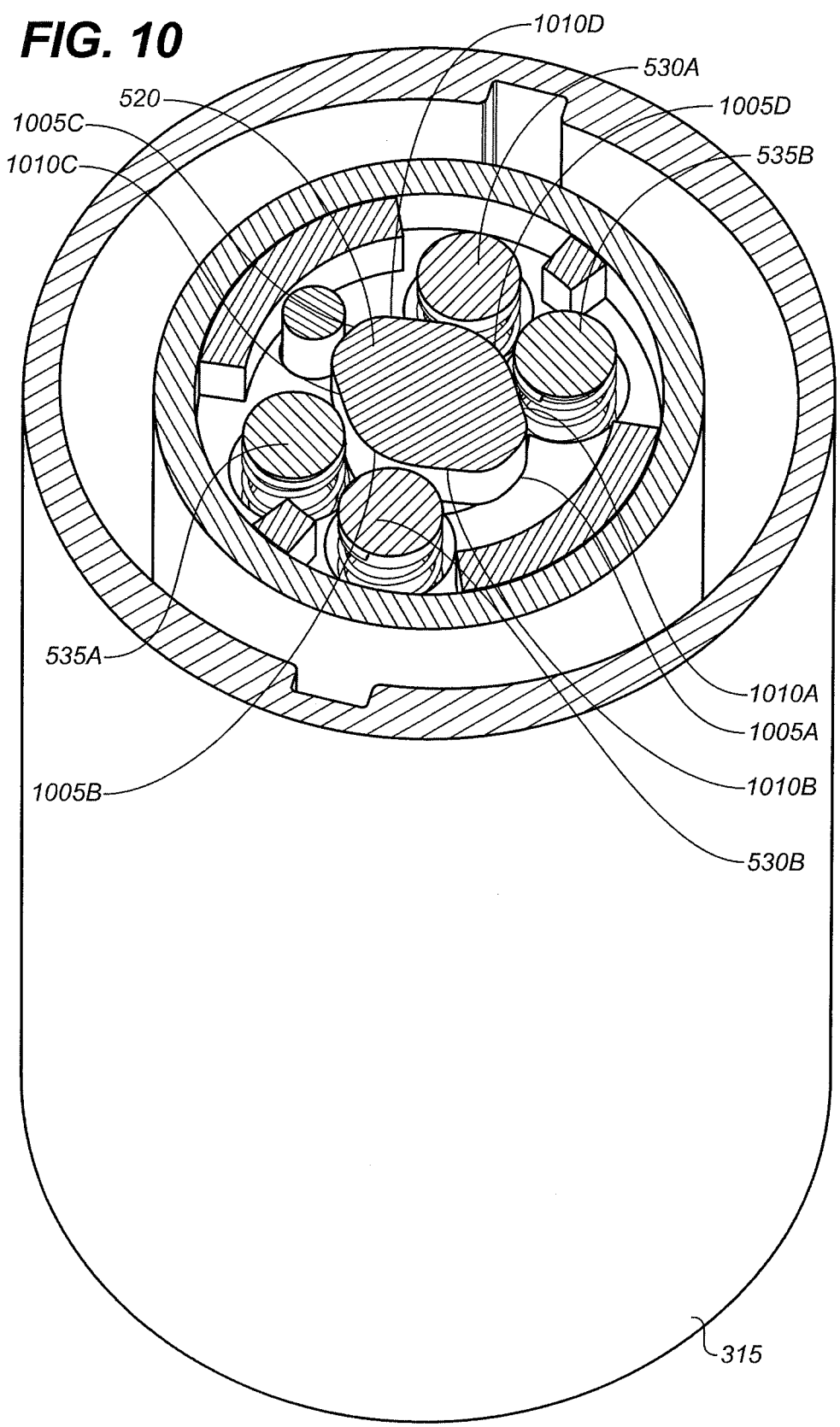
FIG. 10 depicts a sectional view of the valve assembly 445 of FIG. 4 in a closed position, in accordance with an embodiment.

FIG. 10 depicts a sectional view of the valve assembly 445 of FIG. 4 in a closed position, in accordance with an embodiment. The valve assembly 445 includes the check valve ball set one 535 (including the check valve ball one 535A and check valve ball one 535B) and the check valve ball set two 530 (including the check valve ball two 530A and the check valve ball two 530B). As shown, the cam 520, in one embodiment, is rather elliptical in shape, with lobes 1005A, 1005B, 1005C, and 1005D (hereinafter, "lobes 1005") and grooves 1010A, 1010B, 1010C, and 1010D (hereinafter, "grooves 1010"). The elliptical shape, along with the lobes 1005 and the grooves 1010, enables the cam 520, once rotated, to push against and unseat the check valve balls within the check valves. It should be appreciated that the cam 520 may be of any shape that enables the cam 520, once rotated, to unseat the check valve balls of the check valves, thereby opening up the check valve such that fluid may flow there through. FIG. 10 shows the valve assembly 445 such that the cam 520 does not touch or push against any of the check valves of the valve assembly 445, thereby creating the "closed" position.

Figure 11:
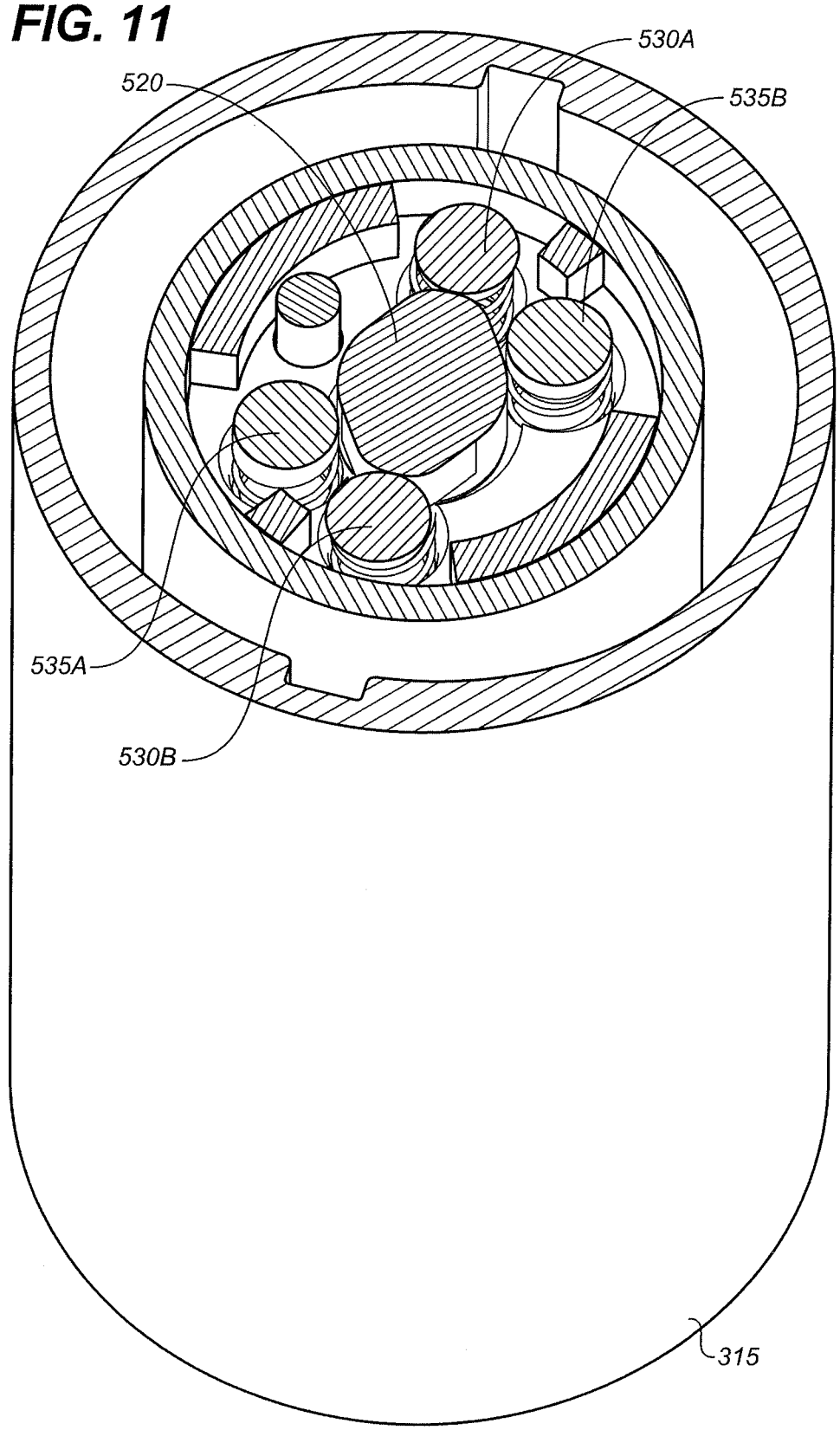
FIG. 11 depicts a sectional view of the valve assembly 445 of FIG. 4 in a compression position, in accordance with an embodiment.

FIG. 11 depicts a sectional view of the valve assembly 445 of FIG. 4 in a compression position, in accordance with an embodiment. As shown, the valve assembly 445 includes the check valve ball set one 535 and the check valve ball set two 530. FIG. 11 shows the valve assembly 445 such that the cam 520 is touching and unseating both of the check valve balls of the check valve ball set two 530. As described herein, after receiving a compression position instruction from the rider, the cam 520 is actuated such that the cam 520 rotates and causes the check valve ball set two 530 to become unseated, thereby attaining the "open" position.

Figure 12:
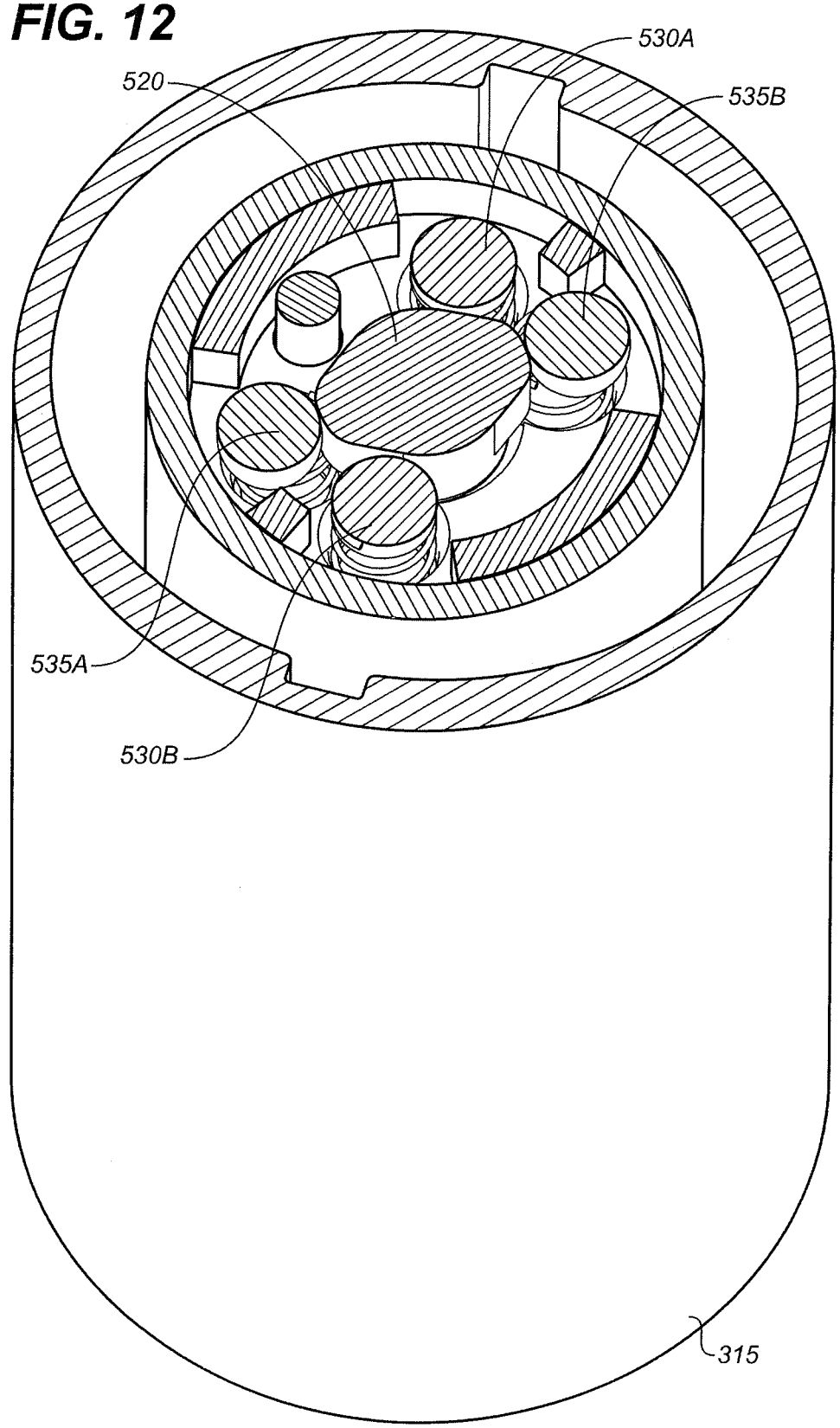
FIG. 12 depicts a sectional view of the valve assembly 445 of FIG. 4 in an extension position, in accordance with an embodiment.

FIG. 12 depicts a sectional view of the valve assembly 445 of FIG. 4 in an extension position, in accordance with an embodiment. As shown, the valve assembly 445 includes the check valve ball set one 535 and the check valve ball set two 530. FIG. 12 shows the valve assembly 445 such that the cam 520 is touching and unseating both of the check valve balls of the check valve ball set one 535. As described herein, after receiving an extension position instruction from the rider, the cam 520 is actuated such that the cam 520 rotates and causes the check valve ball set one 535 to be become unseated, thereby attaining the "open" position.

Figure 13:
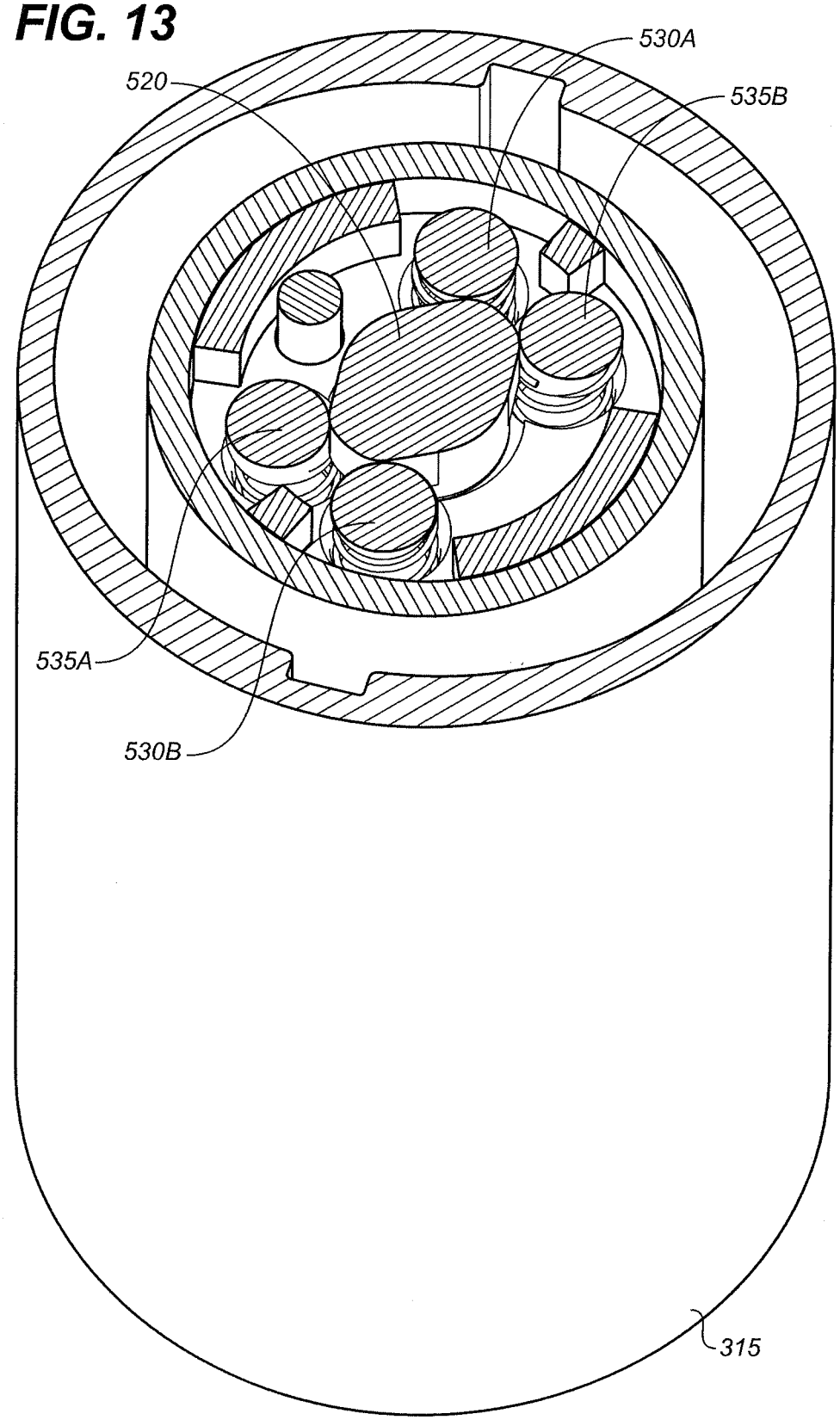
FIG. 13 depicts a sectional view of the valve assembly 445 of FIG. 4 in a full-open position, in accordance with an embodiment.

FIG. 13 depicts a sectional view of the valve assembly 445 of FIG. 4 in a full-open position, in accordance with an embodiment. As shown, the valve assembly 445 includes the check valve ball set one 535 and the check valve ball set two 530. FIG. 13 shows the valve assembly 445 such that the cam 520 is touching and unseating both of the check valve balls of the check valve ball set one 535 and the check valve ball set two 530. After receiving an instruction from the rider to enable an infinitely adjustable seat post position, the cam 520 is actuated such that the cam 520 rotates and cause the check valve ball set one 535 and the check valve ball set two 530 to become unseated, thereby attaining the "open" position for both check valve ball sets. When both the check valve ball set one 535 and the check valve ball set two 530 are unseated and in the open position, the seat post 300 may compress or extend.

Thus, while riding, the rider may actuate the set of control levers 205, causing the check valves to shift to one of the four possible position settings. For example, the controller 370 of motive source M 365 is enabled to determine the following seat post positional instructions from different positions of the levers of the set of control levers 205: an up position; a middle position; a down position; and an infinite position mode setting enabling the transition to any number of positions. In this example, the "up position" instruction consists of the rider pushing on the first control lever 205A once. The "middle position" instruction consists of the rider pushing on the first control lever 205A twice in a short time frame of one second or less. The "down position" instruction consists of the rider pushing on the first control lever 205A three times in a short time frame of one second or less. The "infinite position mode setting" instruction consists of the rider pushing on the second control lever 205B once. It should be understood that the foregoing example is just one design profile for a set of control levers. There may be any number and combination of ways in which the actuating switches and/or buttons representing the different position modes may be designed.

Thus, if the seat post 300 is already in a fully extended position and the rider wants the seat post 300 to compress to the preprogrammed middle position, then the rider pushes on the first control lever 205A twice within a second or less time period. The motive source M 365 receives the "middle position" instruction. The controller 370 of the motive source M 365 is preprogrammed to recognize the middle position instruction via the receipt of a signal, transmitted through the electrical wire 360 or through wireless capabilities.

In one embodiment, a switch 390 is coupled to the vehicle (e.g., bicycle). The switch 390 enables a user to reprogram embodiments to only operate in either the infinite positioning seat post height mode or the finite positioning seat post height mode. The switch 390 is essentially an accessory that may be acquired separate from the system described herein. Various embodiments also include a switch information receiver 395 coupled with the controller 370. In one embodiment, the switch information receiver 395 receives reprogramming information from the switch 390. In one embodiment, the controller 370 receives the information received by the switch information receiver 395 and processes this information as seat post height instructions.

Figure 14A:
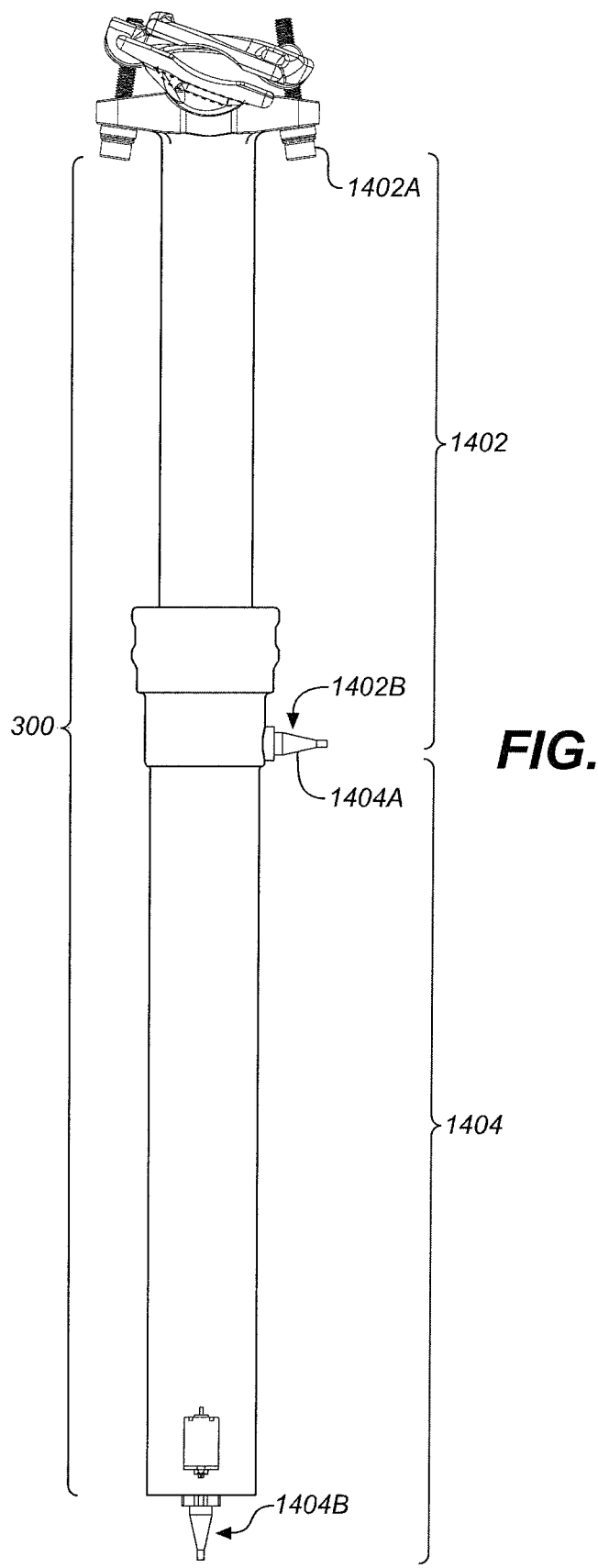
FIG. 14A depicts an antenna coupled with a seat post, in accordance with an embodiment.

FIG. 14A depicts an antenna coupled with the seat post 300, in accordance with an embodiment. In one embodiment, the seat post 300 includes an antenna positioned on the outside of the seat post 300. As can be seen in FIG. 14A, in various embodiments, the antenna 1402 may be in at least two different locations on the seat post 300: the antenna 1402A mounted at the top of the lower post 315; and the antenna 1402B mounted at the top of the upper post 310. The antennae 1402 assist in receiving signals transmitted from any electronic remote controller 355 or electronic controller 325 to the motive source M 365. Only one of the two antennae 1402A and 1402B is required for wireless transmission of signals to the seat post 300. It should be appreciated that the locations at the top of the lower post 315 and the top of the upper post 310 are desirable as the seat post 300 may be installed in a metal bicycle frame. The antennae need to be in a location such that the signal will not be attenuated by the bicycle frame. Of note, FIG. 14A also shows possible power connector locations, 1404A and 1404B (hereinafter, 1404, unless otherwise noted.) The locations of the power connector 1404 operate to enable a location on the seat post 300 at which power may be supplied. Otherwise, a cable (including electrical and/or mechanical wiring) is attached to the outside of the upper post 310, which moves with the upper post 310 during the functioning (adjusting) of the adjustable seat post. This attachment of the cable to the seat post from the battery can cause an excess of cable to occur during compression of the seat post, for example, if the battery is mounted to the bicycle frame. The excess cable may be caught on elements of the rider or the passing terrain, causing inconvenience and/or damage to the bicycle.

Once the controller 370 recognizes a valid instruction sent from the set of control levers 205, then the controller 370 causes the motive source M 365 to direct the motor output shaft 515 to rotate, thereby rotating the cam 520 attached to the motor output shaft 515. The cam 520, in keeping with the instruction to cause the compression of the seat post 300, rotates such that the check valve ball set two 530 is unseated, thereby allowing fluid flow there through, as was described herein. The rider, concurrently, sits on the saddle to cause the check valve ball set one 535 of the check valve one 510 to unseat, thereby creating a free flow of fluid through the check valve one 510 and check valve two 525.

Once the controller 370 determines that the seat post 300 has reached its intended position, the motive source M 365 signals to the motor output shaft 515 to rotate in a certain direction and number of degrees such that the attached cam 520 rotates to attain the "closed position" (in which none of the check valve balls of the check valves are unseated) described with respect to FIG. 10.

In one embodiment, an audible and/or visual (e.g., LED) indicator provides an indication (to the user) that the seat post 300 has reached its intended position. For example, an audible indicator may provide various preprogrammed noises for various lengths of time and at various noise levels corresponding to the up, middle, and down positions of the seat post 300. In another example, the visual indicator may provide various preprogrammed lights for various lengths of time and at various intensities. In various embodiments, the audible and visual indicators are coupled to and receive, via wire and/or wirelessly, activation instructions from the controller 370. The activation instructions direct the devices with the audible and visual indicators to provide the associated indication.

In one embodiment, the controller 370 is preprogrammed to recognize an instruction from the rider, via the set of control levers 205, directing the seat post 300 to only move in one direction (either up or down) regardless of the amount of force exerted upon it. Thus, if the rider is sitting on the saddle and the controller 370 has received an "extension position" instruction, the seat post 300 will not move downwards, regardless of the force with which the rider is sitting on the saddle. Conversely, if the rider is riding standing on the pedals and the controller 370 has received a "compression position" instruction, the seat post 300 will not move upwards, unless the rider overcomes the force preventing the extension when pulling up on the seat post 300; there is a limited amount of force preventing extension that is a function of the internal pressure in the pressurized air chamber 420 times the annular area between the inner tube one 460 and outer tube two 435. The air spring internal to the seat post 300 cannot cause an extension when the check valve 510 is closed, but the rider could conceivably overcome this force by pulling on the saddle, although it is undesirable that this would occur. The design intent is that the seat post 300 would not extend when the check valve 510 is closed.

In another embodiment, the controller 370 is preprogrammed to receive instructions from a voice activated audio detection module 380 mounted on the handlebar 200 or some other area of the bicycle, in which the voice activated audio detection module 380 receives audible position instructions from the rider and translates and transmits these instructions to the controller 370. In other words, the voice activated audio detection module is preprogrammed to receive a coded language and transmit the received coded language in the form of a position instruction. In this embodiment, the voice activated audio detection module 380 is positioned separate from the set of control levers 205 (which may include any of the following: an electronic remote controller 355; a mechanical remote controller 345; and an electronic controller 325). In one embodiment, the controller 370 is capable of receiving and translating audible "position" instructions such that the motive source M 365 passes on these instructions to the motor output shaft 515. In another embodiment, the set of control levers 205 includes a voice activated audio detection module 380.

Of significance, in embodiments, the controller 370 of the motive source M 365 is preprogrammed to recognize an "infinite position" mode instruction from the rider. Upon receiving this infinite mode instruction, the motive source M 365 directs the motor output shaft 515 to rotate in a certain direction and number of degrees such that the attached cam 520 rotate to attain the "fully open position", as was described with respect to FIG. 13.

In one embodiment, a proportional-integral-derivative controller (PID controller) is coupled to the motive source M 365. PID controllers are commonly known in the industry. Additionally, embodiments also include an angle sensor and a gear reduction coupled to the motive source M 365, as well as a displacement sensor (e.g., pressure sensor 570). The angle sensor determines the position of the motive source M 365. The gear reduction is able to increase or decrease the rate of work of the gears of the motive source M 365. Typically, the gear reduction is constant and the output speed of the motor output shaft 515 is controlled with electrical current. A variable transmission may also perform the same function, in some situations. The displacement sensor calculates how close the seat post is to the desired set position. This displacement information is used as feedback to the controller 370. In application to embodiments, the PID controller enables, among other things, the system to determine when (proportional control) and how fast (integral control) to close the check valves. The PID controller calculates the "error" value as the difference between the actual position of the seat post 300 and the desired position of the seat post 300. The PID controller attempts to minimize this error (difference in positions) by adjusting the process control inputs, causing the cam 520 to rotate at the same pace as previous rotations, but with the intent to reduce or eliminate the measured positional gap to achieve as close a value to zero as possible.

Figure 14B:
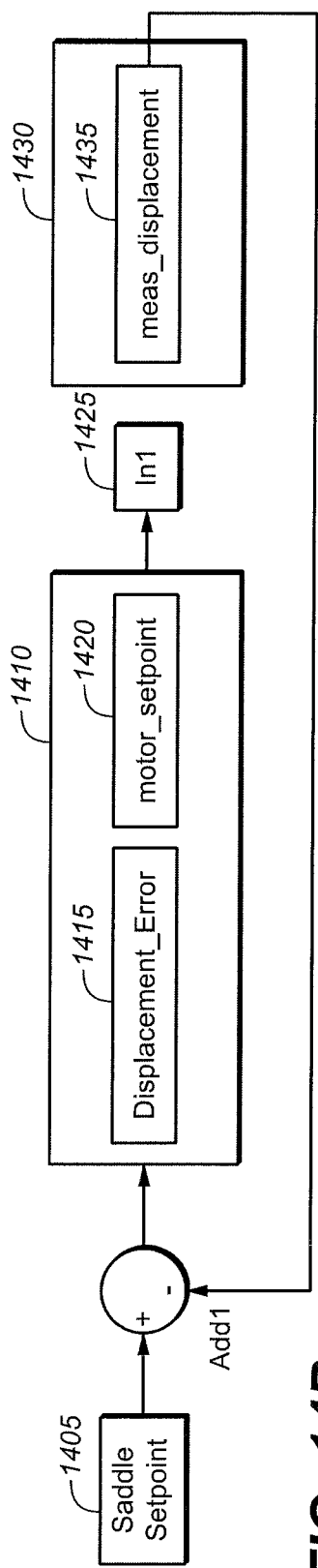
FIG. 14B depicts a circuit drawing including a proportional-integral-derivative controller ("PID controller") 1410, in accordance with an embodiment.

FIG. 14B depicts a circuit drawing 1400 including a PID controller 1410, in accordance with an embodiment. In an example operation scenario, with reference to a first feedback loop of two feedback loops, the operation of which will be described herein, the PID controller 1410 receives a compression position instruction (represented by "signal 1") 1405, which would be considered to be the desired position of the seat post 300. Then a displacement sensor calculates the actual position (represented by "signal 2") of the seat post 300. Signal 1 is subtracted from signal 2, to attain the displacement error measurement 1415. The PID controller 1410 uses this error measurement to determine a solution (motor setpoint 1420) to reduce or eliminate the measured difference such that the seat post 300 arrives at the desired location at the desired time. Solutions may include, but are not limited to being the following: a proportional control solution (e.g., the motive source M 365 causing the rotation of the cam 520 to occur in a certain number of degrees in a certain direction at a steady rate); and an integral control solution (e.g., the motive source M 365 causing the rotation of the cam 520 a certain number of degrees in a certain direction at a speed that is determined to reduce or eliminate the error). During operation, the speed may be controlled by beginning to rotate the cam and close a check valve set, the speed at which the seat post 300 moves may be controlled.

The motor setpoint 1420 then is fed into the motor angle controller 1425 (coupled with the motive source M 365), which has its own feedback (PID) loop (the second PID loop) with an encoder. Using the second PID loop, the encoder receives the signal from the PID controller 1410 and translates this signal by applying a conversion angle measurement to the number of bits and the degrees of the motor setpoint 1420. The motor angle controller 1425 determines which direction and how fast the motive source M 365 (and hence the cam 520) should move in order to minimize or eliminate the measured (angular) displacement error between the motor angular position and the motor angular set point.

Thus, using the PID controller 1410, embodiments are able to cause the motive source M 365 to spin slower as the setpoint (desired) point is getting closer. As such, in some embodiments, the motive source M 365 and the attached controller 370 cause the motor output shaft 515 to rotate in such a way according to compression and/or extension instructions such that the valve assembly 445 moves to some position between open and close, thereby slowing the movement of the seat post 300 to the desired position.

Thus, using the two feedback loops, the PID controller 1410 is able to assist in tuning the check valve openings by instructing the motive source M 365 to cause the motor output shaft 515 to rotate in a certain direction and speed. The displacement transducer 1430 takes the measured displacement 1435 (including information associated with the displacement sensor and the motor angle controller [measuring angular displacement]) and converts it into a voltage, which essentially gets converted into a valve assembly position (e.g., compression position; extension position).

Of note, the PID controller 1410 may be used for any type of electromechanical seat post, including a seat post using hydraulic valves.

Figure 16:
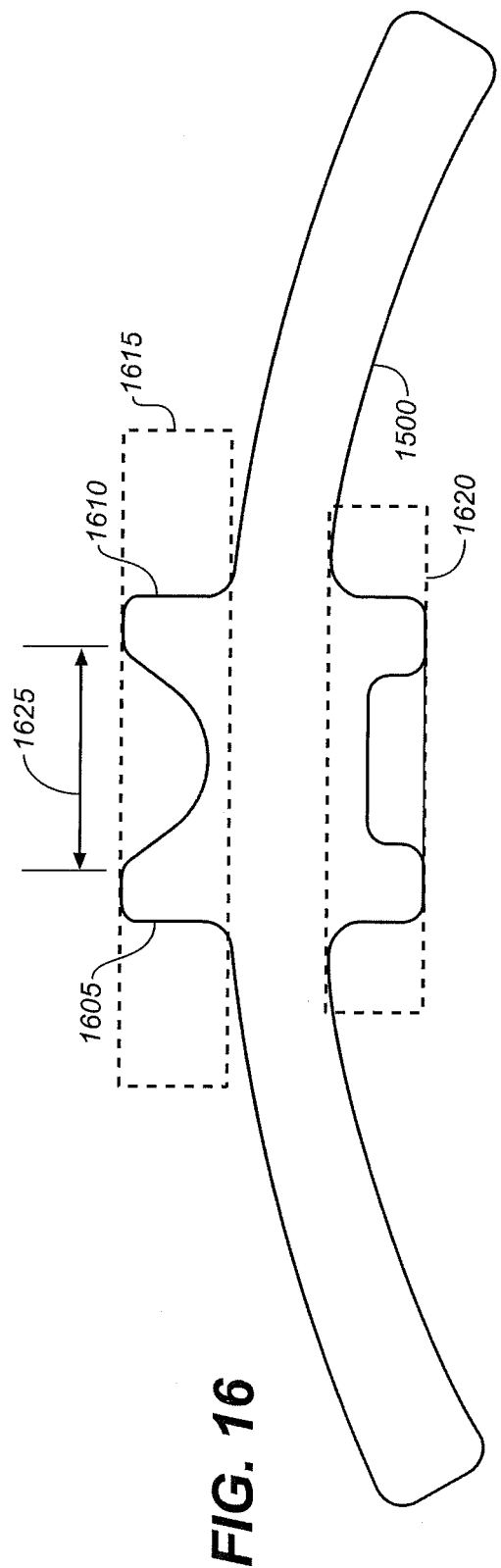
FIG. 16 shows an enlarged view of the bushing 1500 of FIG. 15, in accordance with an embodiment.
Figure 15:
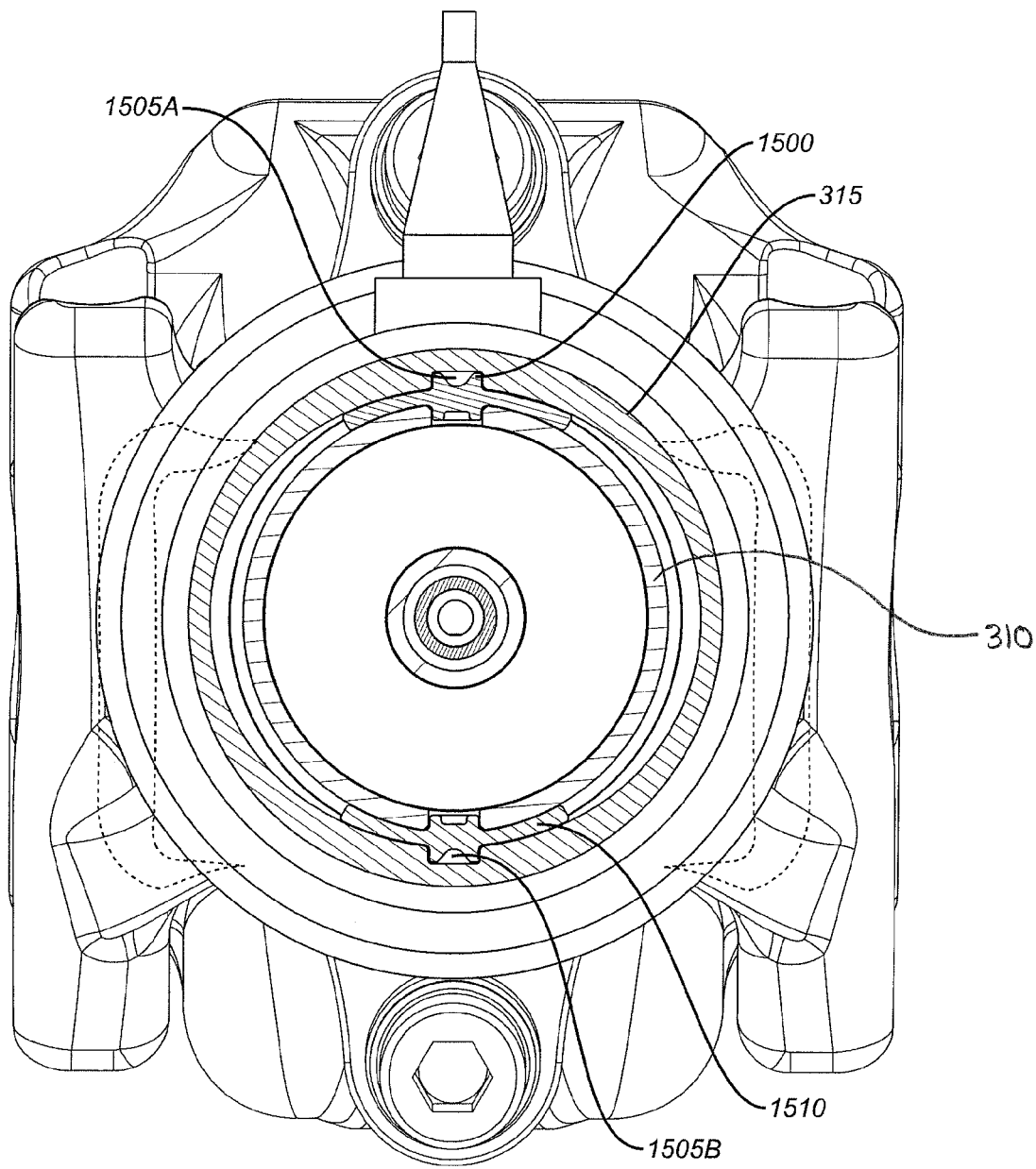
FIG. 15 depicts a sectional view of a bushing for preventing rotational slop between the upper post and the lower post, in accordance with an embodiment.

FIG. 15 depicts a sectional view of a bushing for preventing rotational slop between the upper post and the lower post, in accordance with an embodiment. FIG. 16 depicts an enlarged view of the bushing 1500 of FIG. 15, in accordance with an embodiment.

FIG. 15 shows the upper post 310 telescopically engaged with the lower post 315. A gap normally exists in between the upper post 310 and the lower post 315, causing play with the seat post 300 and the saddle. Embodiments provide for at least one bushing 1500 to be placed in at least one slot 1505A formed within the upper post 310 and the lower post 315. This bushing 1500 has anti-rotation capabilities; the bushings 1500 and 1510 are inserted into the slots 1505A and 1505B of the upper post 310 and the lower post 315, respectively, such that there is little or no rotational play between the upper post 310 and the lower post 315.

The bushings 1500 and 1510 installed within the slots 1505A and 1505B of the upper post 310 and the lower post 315, respectively, help reduce and/or eliminate rotation about the seat post axis between the upper and lower post.

In one embodiment, the bushing is preloaded. By preloaded, it is meant that the bushing contains a split in its design such that the bushing applies pressure to the sides of the slots when installed within the upper post and the lower post. FIG. 15 shows the bushing 1500 is lodged within the slot 1505A of the upper post 310 and the bushing 1510 is lodged within the slot 1505B of the lower post 315. In one embodiment, the slots 1505A and 1505B within which the bushings 1500 and 1510, respectively, are placed are smaller than the bushings 1500 and 1510, respectively, themselves. This size differential, along with the split design, causes the bushings 1500 and 1510 to securely hold in place the upper post 310 and the lower post 315 such that the upper post and the lower post, 310 and 315, respectively, do not rotate relative to each other about the seat post axis. The bushings 1500 and 1510 with the split design more securely hold in place the upper post and the lower post, 310 and 315, respectively, because the two arms of the bushings, for example, first arm 1605 and second arm 1610 of the bushing 1500 push outward against the walls of the slot 1505A. It should be appreciated that the first arm 1605 and the second arm 1610 may be any shape that is capable of having a gap there between and capable of having a pre-load due to this gap. In one embodiment, the first side 1615 of the bushing, for example, bushing 1500, is attached to the lower post 315, while the second side 1620 of the bushing 1500 is attached to the upper post 310. In another embodiment, the first side 1615 of the bushing 1500, is attached to the upper post 310, while the second side 1620 of the bushing 1500 is attached to the lower post 315.

It should be appreciated that in various embodiments, one or both of the first side 1615 and the second side 1620 of the bushing, for example, bushing 1500, may be of a split design. Further, the preload for the split bushing may be adjusted by adjusting the gap between the arms of the bushing. For example, with reference to bushing 1500 of FIG. 16, if the gap 1625 was enlarged, then the preload value would increase. If the gap 1625 was reduced, then the preload value would decrease.

Figure 17:
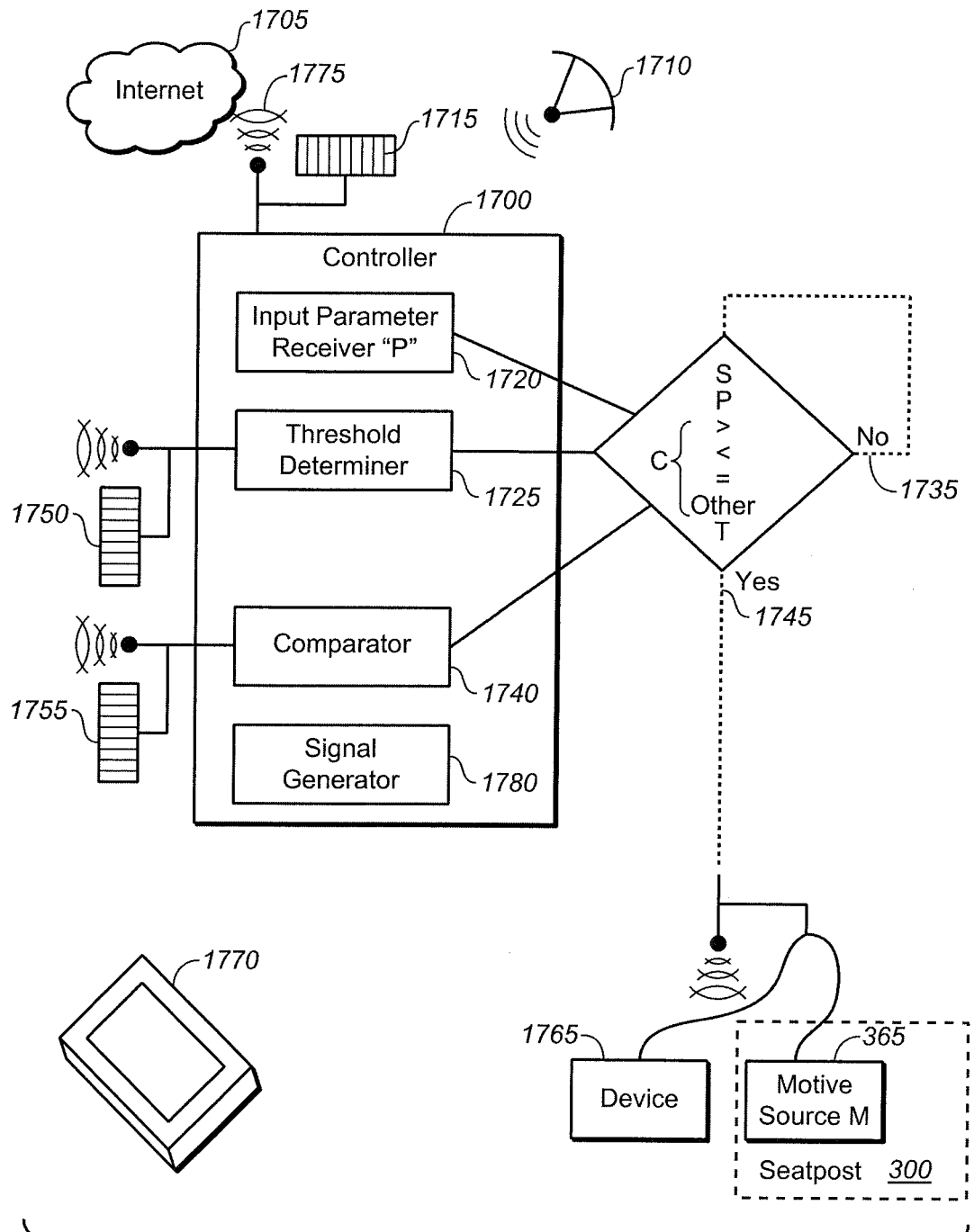
FIG. 17 depicts a controller coupled with a motive source M of a seat post, in accordance with an embodiment.

FIG. 17 depicts a controller coupled with the motive source M 365 (e.g., power source such as a battery), in accordance with an embodiment. In one embodiment, the motive source M 365 is part of other components, such as, but not limited to, the seat post 300, a suspension, and a drive train. In one embodiment, the controller 1700 is capable of receiving and processing communication from a GPS system. A cyclist makes seat post height and/or shifting decisions based on encountered terrain. Currently, technology allows an onboard computer equipped with GPS to indicate and record where the cyclist/bicycle is on the globe varies accurately. Trail/route mapping downloading and uploading is possible as a result of this technology. In one embodiment, the GPS driven terrain knowledge (e.g. terrain variation at a GPS known location) can also be used to make bicycle seat post height and shifting decisions. When following a pre-mapped route, for example, predetermined seat post height and/or gear selections, or suspension settings can be embedded in the route map and the controller can signal the seat post height changer and gear changer to change to the location appropriate seat post height and/or shift to the location appropriate gear automatically.

With reference to FIG. 17, in one embodiment, a system for automatically triggering seat post height changes includes at least the following: an electro mechanical bicycle seat post height changing system; a cyclist performance measuring device; an on board (on the cyclist or the bicycle) computer/controller 1700; computer/controller software; wireless communication between a mobile device 1770 [e.g., smart phone] and the computer/controller 1700 and/or the ability to connect the computer/controller 1700 to a laptop/desktop computer; configurable shifting points/thresholds 1725 configurable via the mobile device 1770 wireless communication based on GPS 1710 and/or performance measuring device signals 1775.

Embodiments also provide the ability to record a GPS route so that the system remembers where the user moves the seat post, shifts, changes suspension settings, etc., during a ride along a certain route. Then, the next time the user rides on that route, based on the GPS location, embodiments automatically adjust the settings to where the rider had previously set them. It should be appreciated that the computer/controller may also be used in conjunction with an electro mechanical bicycle shifting system.

In one embodiment, the bicycle includes adjustable suspension (front and rear or front or rear as preferred), including adjustable damping and/or spring load and an adjustable seat post. The combined adjustability results in a completely adjustable bicycle that can be tailored regarding initial suspension sag setting, spring rates, damping rates, and seat post height or any portion of those depending on rider preference and terrain requirements.

Manually operated electro mechanical bicycle shifting systems exist in the bicycle industry and have been commercialized by at least SHIMANO and Campagnolo. Certain of such shifting technology are described, for example, in United States patent application publication number 2005/0227798 A1 to Shimano and U.S. Pat. No. 7,874,567, each of which is entirely incorporated herein by reference.

Various cycling performance measuring devices are ASAP commercialized in the bicycle industry such as cyclist power output meters, cyclist torque meters, heart rate monitors, etc. . . . Some human (e.g., heart rate) physiological monitors are described, for example, in U.S. Pat. Nos. 7,764,990, 4,938,228, and 7,927,253, each of which is entirely incorporated herein by reference. Some cycle torque meters are described, for example, in U.S. Pat. Nos. 7,775,128, 8m141m438m and 4,630,818, each of which is entirely incorporated herein by reference.

These performance measuring devices may communicate wirelessly to an on board cycling computer or various handheld devices (e.g., iPhone, tablet computer) for real time, feedback to the cyclist. These measuring devices may also record the data captured for later downloading to a less mobile device such as a desktop computer or internet storage/computing location, for later data evaluation.

Embodiments utilize the various methods and devices for measuring heart rate/power/torque from a cyclist to trigger electromechanical shifting and/or seat post height changes to occur as a real time monitor measures. For example, any or all of heart rate, power, and/or torque upper and lower limits can be used in conjunction with an electro mechanical shifting system and/or an electromechanical seat post height changing system, to cause the shifting systems to shift gears and/or the change the seat post height in order to maintain a preset power, torque, or heart rate for the cyclist. Ranges for one or more performance measures (E.G., heart rate, torque) are utilized as thresholds for signaling a gear change when outside of a predetermined range or trigger point for a given performance measure. If the cyclist's subject performance measures, or combination of measures falls above or below the preconfigured trigger point, shifting and/or seat post height changes will automatically occur to insure the cyclist remains within the preset performance measure ranges.

Referring to an embodiment shown in FIG. 17, the controller 1700 includes at least the following components: an input parameter receiver 1720; a threshold determiner 1725; a comparator 1740; and a signal generator 1780. The input parameter receiver 1720 receives input that includes at least one input parameter receiver 1720 with memory (multiple inputs are optional) such that the input parameters or sensed/measured parameters (e.g., real time heart rate, torque, other from appropriate sensor) is buffered into the controller 1700. The controller 1700 includes a threshold determiner 1725 that is configured for determining is a threshold has been met and/or exceeded. The threshold determiner 1725 is also configured for receiving a threshold value or range (for the chosen parameter) as input, which threshold value or range may then be stored at the controller 1700 or at some other memory storage. The controller 1700 further includes a comparator 1740 configured for comparing the input received by the input parameter receiver 1720 and the threshold determination determined by the threshold determiner 1725. The comparison (or operator function input) can be stored at the controller 1700 or at some other memory storage. In one embodiment, the user inputs a chosen threshold for heart rate (for example) such that the threshold is 150 beats/minute. The comparator 1740 receives input that the comparison value that should be considered is that of "greater than or equal to" (see potential comparison inputs 1730). The input parameter receiver 1720 is connected by wire or wirelessly (e.g., Bluetooth) to a heart rate monitor. The signal generator 1780 (output port) (the signal generator 1780 is configured for generating a signal based on the comparison performed by the comparator 1740) is connected to, for example, a device 1765 (e.g., electric gear changer [e.g., gear shift, Shimano Di-2]) and/or the motive source M 365.

When the heart beat detected by the input parameter receiver 1720 equals or exceeds 150 beats/min. (see 1745, "yes", of FIG. 17), the controller 1700, having been continuously comparing the parameter input and the threshold information by the comparator 1740, sends an output signal 1760 to the gears signaling the change to decrease the gear ratio by one shift. In another embodiment, the controller 1700, sends an output signal 1760 to the motive source M 365, signaling a seat post height change. If the heart beat detected by the input parameter receiver 1720 is less than the 150 beats/min. threshold (see 1735, "no", of FIG. 17), then the controller 1700 does not send an output signal 1760, but continues to monitor the input parameters (and hence the input parameter receiver 1720), the threshold determiner 1725, and the comparator 1740. Of note, the threshold determiner 1725 is connected to, either through wire or wirelessly, an external device 1750 capable of communicating therewith. Further, the comparator 1740 is connected to, either through wire or wirelessly, an external device 1755 capable of communicating therewith. Additionally, FIG. 17 shows an embodiment with adjustment knob 1715, configured for adjusting the input parameter(s) that the input parameter receiver 1720 should receiver.

In one embodiment, a stabilization time delay circuit is included (e.g., three minutes) in the controller 1700 that suspends further controller action for a predetermined (and settable) amount of time to allow the parameter to adjust based on the recent gear change and/or seat post height change.

The controller 1700 and performance measurement triggers described herein may, in one embodiment, be used to control and dynamically configure suspension components having electrically actuated configuration systems operable therewith.

Referring again to FIG. 17, the controller 1700 may be configurable and/or may output via a mobile phone application, communication with the internet 1705, based on stored data corresponding to real time GPS input, manually, or any suitable combination thereof.

In one embodiment, the gear shifting system includes: the controller 1700; the gear shifter device 1765 in communication with the controller 1700; and a performance sensor in communication with the controller 1700. In another embodiment, a suspension modification system includes: the controller 1700; a suspension device in communication with the controller 1700; and a performance sensor in communication with the controller 1700.

Referring now to FIGS. 1-17, one embodiment provides for a dropper seat post that includes the seat post 300. Further, the seat post 300 includes: the upper post 310; the lower post 315 within which said upper post telescopically slides; and the valve assembly 445 configured for regulating fluid flow within a variable finite positioning seat post height mode in response to seat post height instructions received by said seat post 300.

In one embodiment, the valve assembly 445 is positioned internal to the lower post 315. In another embodiment, the valve assembly 445 is positioned external to the lower post 315. In one embodiment, the valve assembly 445 is positioned internal to the upper post 310.

In one embodiment, the seat post 300 of the dropper seat post further includes the motive source 365, described herein, coupled with the valve assembly 445. The motive source 365 includes a controller configured for receiving the seat post height instructions and determining a real-time displacement measurement, wherein the real-time displacement measurement is based on a measured difference between a seat post height position of the received seat post height position instructions and a real-time seat post height of the seat post 300. In one embodiment, the controller is further configured for proportionally controlling, based on the real-time displacement measurement, at least one of rate and timing of at least one of the opening and closing of check valves of the valve assembly 445.

Various additional embodiments provide for a dropper seat post system that includes the following: a user interface (described herein) coupled to a vehicle; the seat post 300 described herein; and at least one controller coupled to a motive source M 365 described herein. The user interface is configured for receiving a pattern of touches representing a seat post height position instruction, wherein the seat post height position instruction comprises one of: an infinite positioning seat post height mode; and a finite positioning seat post height mode. The seat post 300 is coupled to the vehicle and is separate from the user interface. The seat post 300 includes: the upper post 310; the lower post 315 within which the upper post telescopically slides; and at least one controller coupled with a motive source, said motive source positioned in said lower post, said at least one controller (such as controller 370) configured for receiving the seat post height position instruction and signaling for a movement of the seat post 300 in accordance with the seat post height position instruction.

In one embodiment, the user interface of the dropper seat post system includes a set of control levers, wherein the set of control levers includes at least one actuatable trigger configured for receiving the pattern of touches representing the seat post height position instruction.

In one embodiment, the seat post 300 of the dropper seat post system includes a valve assembly 445 configured for transitioning between an infinite and a finite positioning seat post height mode. In one embodiment, the valve assembly 445 is positioned internal to the lower post 315. In another embodiment, the valve assembly 445 is positioned external to the lower post 315. In yet another embodiment, the valve assembly 445 is positioned internal to the upper post 310.

In one embodiment, the at least one controller (e.g., controller 370 includes a proportional-integral-derivative controller configured for providing proportional control of an opening and closing of check valves of a valve assembly, wherein a rate and a timing of the opening and the closing of the check valves being in proportion to a real-time displacement measurement associated with the seat post 300.

It should be appreciated that embodiments, as described herein, can be utilized or implemented alone or in combination with one another. While the present invention has been described in particular embodiments, it should be appreciated that the present invention should not be construed as limited by such embodiments, but rather construed according to the following claims.

The invention claimed is:

1. A system comprising:
a seat post, said seat post comprising:
an upper post;
a lower post within which said upper post telescopically slides; and
an anti-rotation bushing positioned in between an upper post and a lower post of said seat post, said anti-rotation bushing configured for stabilizing said seat post in at least one direction;
a user interface operatively connected with said seat post, said user interface configured for receiving instructions associated with a height of said seat post and for communicating received instructions to at least one controller coupled with a motive source of said seat post; and
a valve assembly in communication with said motive source, said valve assembly regulating fluid flow within a variable finite positioning seat post height mode in response to a translation of said received instructions by said motive source.

2. The system of claim 1, wherein said user interface is remote from said valve assembly.

3. The system of claim 2, wherein said user interface comprises at least one of a GUI, button, dial, smart phone, and lever.

4. The system of claim 1, wherein said valve assembly comprises:
at least one set of check valves configured for at least one of opening and closing in response to said translation.

5. The system of claim 4, wherein a rate of said opening and said closing of said at least one set of check valves is proportional to a real-time displacement measurement, wherein said real-time displacement measurement is based on a measured difference between a seat post height position instruction of said received instructions and an actual seat post height of said seat post.

6. The system of claim 4, wherein said at least one set of check valves comprising:
two sets of check valves positioned, relative to each other, in a series, and opposed to each other, such that one-way only movement is achieved in response to said translation.

7. The system of claim 4, further comprising:
a proportional-integral-derivative controller configured for controlling a rate of said opening and said closing of said at least one set of check valves.

8. The system of claim 4, further comprising:
a displacement sensor coupled with said controller, said displacement sensor configured for measuring a displacement between a seat post height position instruction and an actual seat post height of said seat post.

9. The system of claim 8, wherein said displacement sensor is a pressure sensor.

10. The system of claim 1, wherein said user interface comprises:
at least one activation button configured for activating a pre-programmed seat post position, wherein said controller comprises said pre-programmed seat post position.

11. The system of claim 1, wherein said anti-rotation bushing comprises:
a first side; and
a second side, wherein a portion of said first side of said anti-rotation bushing is positioned in a first slot of said upper post and a portion of said second side of said anti-rotation bushing is positioned in a second slot of said lower post.

12. The system of claim 11, wherein at least one of said portion of said first side and said portion of said second side comprises:
a pre-load configuration.

13. The system of claim 12, said pre-load configuration comprising:
a first arm coupled to a body of said anti-rotation bushing; and
a second arm coupled to said body and separated from said first arm by a gap, wherein said first arm, said gap, and said second arm are configured to fit, with pre-load, into at least one of said first slot and said second slot.

14. The system of claim 1, further comprising:
a motor output shaft coupled with said motive source and internal to said seat post, said motor output shaft configured for rotating in response to said translation; and
a cam coupled with said motor output shaft and said valve assembly and internal to said seat post, said cam configured for moving in response to said rotating of said motor output shaft and configured for at least one of seating and unseating at least one check valve ball set.

15. The system of claim 1, wherein said at least one controller comprises:
a proportional-integral-derivative controller.

16. The system of claim 1, further comprising:
at least one antenna coupled to said seat post, said at least one antenna configured for enabling communication between said user interface and said motive source.

17. The system of claim 16, wherein said at least one antenna is coupled to a top of at least one of an upper and a lower post of said seat post.

18. The system of claim 1, further comprising:
at least one power connector location configured for enabling power to be received at said seat post.

19. The system of claim 18, wherein said at least one power connector location is positioned at an upper end of a lower post.

20. The system of claim 1, further comprising:
a switch coupled with said seat post, said switch configured for enabling a reprogramming of said valve assembly to only operate in either one of an infinite positioning seat post height mode or a finite positioning seat post height mode.

21. The system of claim 1, further comprising:
a voice activated audio detection module coupled with said seat post, said voice activated audio detection module configured for receiving audible position instructions, translating said audible position instructions, and transmitting translated audible position instructions to said at least one controller, such that an instruction for a desired position for said seat post is received at said controller.

22. The system of claim 1, wherein said instructions received at said user interface is an audible instruction, wherein said user interface comprises a voice activated audio detection module.

23. The system of claim 1, wherein said at least one controller comprises:
an input parameter receiver configured for receiving an input;
a threshold determiner coupled with said input parameter receiver, said threshold determiner configured for determining whether or not a predetermined threshold has been exceeded; and
a comparator coupled with said threshold determiner, said comparator configured for comparing said input and said threshold; and
a signal generator coupled with said comparator, said signal generator configured for generating a signal based upon said comparing.

24. The system of claim 23, wherein said input is associated with physiological factor relating to a rider of a vehicle that comprises said seat post.

\* \* \* \* \*